United States Patent
Tanaka et al.

[11] Patent Number: 5,807,806
[45] Date of Patent: Sep. 15, 1998

[54] BENZOYLPYRAZOLE DERIVATIVES HAVING SPECIFIC SUBSTITUENTS AND HERBICIDE

[75] Inventors: Katsunori Tanaka; Hiroyuki Adachi; Masami Koguchi, all of Odawara; Takashi Kawana, Ohi, all of Japan

[73] Assignee: Nippon Soda Co., Ltd., Tokyo, Japan

[21] Appl. No.: 922,143

[22] Filed: Aug. 25, 1997

[51] Int. Cl.⁶ .................................................. C07D 231/20
[52] U.S. Cl. .................. 504/282; 548/373.1; 548/374.1; 548/376.1
[58] Field of Search .................. 504/282; 548/373.1, 548/374.1, 376.1

[56] References Cited

U.S. PATENT DOCUMENTS 4,948,887  8/1990  Baba et al. ............................. 540/603

FOREIGN PATENT DOCUMENTS

| 0 282 944 A2 | 3/1988 | European Pat. Off. . |
| WO 96/26192 | 8/1996 | Germany . |
| WO 96/26193 | 8/1996 | Germany . |
| WO 96/26200 | 8/1996 | Germany . |
| WO 96/26206 | 8/1996 | Germany . |

*Primary Examiner*—Deborah C. Lambkin
*Assistant Examiner*—Jane C. Oswecki
*Attorney, Agent, or Firm*—Joseph C. Mason, Jr.

[57] ABSTRACT

The present invention is directed to a compound of formula (1);

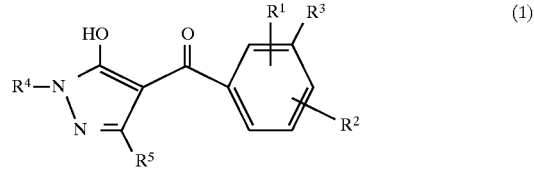

wherein $R^1$ and $R^2$ are each independently a halogen atom, a $C_{1-6}$ alkyl, a $C_{1-6}$ haloalkyl, a $C_{1-6}$ alkylsulfonyl or the like, $R^3$ is a di-$C_{1-6}$ alkoxymethyl, a di-$C_{1-6}$ alkylthiomethyl, and $R^4$ and $R^5$ are each independently hydrogen, a $C_{1-6}$ alkyl, a $C_{2-6}$ alkenyl or the like, and a salt thereof, and a herbicide comprising the said compound and/or the salt.

2 Claims, No Drawings

BENZOYLPYRAZOLE DERIVATIVES HAVING SPECIFIC SUBSTITUENTS AND HERBICIDE

FIELD OF THE INVENTION

The present invention relates to novel a benzoylpyrazole derivative having a specific substituent and a herbicide comprising said benzoylpyrazole derivative as its active component.

BACKGROUND ART

As a herbicide comprising a compound having a pyrazole skeleton wherein a benzoyl group is substituted to the 4th position of a pyrazole ring, the following compound of formula (I);

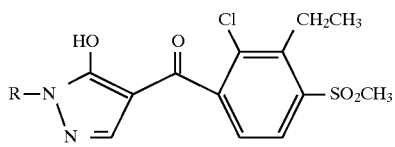

is disclosed in Japanese Patent Laid-open No. Hei 2-173 Gazette, and another compound of formula (II);

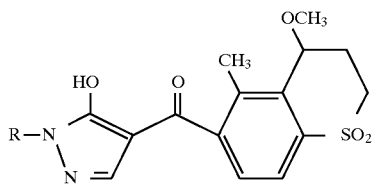

is disclosed in Japanese Patent Laid-open No. Hei 7-309869 Gazette.

Further, in WO 96/26206 Gazette, a compound of formula [III];

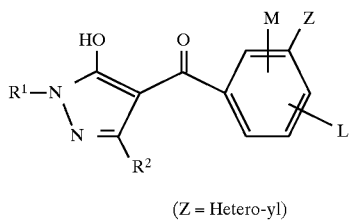

(Z = Hetero-yl)

is also disclosed.

It is an object of the present invention to provide a herbicide which can be advantageously manufactured in an industrial scale, having firm herbicidal activity at a lower dose thereof and having excellent selectivity in its herbicidal activity that does not give harmful effect on crops.

DISCLOSURE OF THE INVENTION

The present invention is directed to a compound of formula (I);

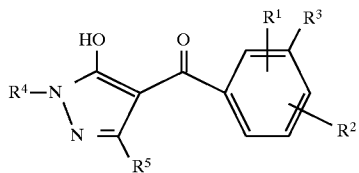

wherein $R^1$ and $R^2$ are each independently hydrogen, a halogen atom, nitro, cyano, a $C_{1-6}$ alkyl, a $C_{1-6}$ alkoxy, a $C_{1-6}$ haloalkyl, a $C_{1-6}$ haloalkoxy, a $C_{1-6}$ alkylthio, a $C_{1-6}$ alkylsulfinyl or a $C_{1-6}$ alkylsulfonyl;

$R^3$ is formyl, a di-$C_{1-6}$ alkoxymethyl or a di-$C_{1-6}$ alkoxythiomethyl;

$R^4$ and $R^5$ are each independently hydrogen, a $C_{1-6}$ alkyl, a $C_{1-6}$ haloalkyl, a $C_{2-6}$ alkenyl, a $C_{2-6}$ alkynyl or a $C_{3-8}$ cycloalkyl, or a salt thereof, and a herbicide comprising said compound(s) or said salt(s) thereof.

As an example for the halogen atom represented by $R^1$ and $R^2$, chlorine, bromine, fluorine and the like are given. In addition, as an example for the $C_{1-6}$ alkyl represented by the same, methyl, ethyl, propyl, isopropyl, butyl, s-butyl, t-butyl and the like are given; as an example for the $C_{1-6}$ alkoxy, methoxy, ethoxy, propoxy, isopropoxy, butoxy, t-butoxy and the like are given; as an example for the $C_{1-6}$ haloalkyl, fluoromethyl, 1-fluoroethyl, 2-fluoroethyl, difluoromethyl, trifluoromethyl, difluorochloromethyl, fluorochloromethyl, trichloromethyl, tribromomethyl, trifluoroethyl, pentafluoroethyl and the like are given; and as an example for the $C_{1-6}$ haloalkoxy, trifluoromethoxy, 1,1,2,2-tetrafluoroethoxy, trichloromethoxy, difluoromethoxy and the like are given. Furthermore, as an example for the $C_{1-6}$ alkylthio, methylthio, ethylthio, propylthio, isopropylthio and the like are given; as an example for the $C_{1-6}$ alkylsulfinyl, methylsulfinyl, ethylsulfinyl and the like are given; and as an example for the $C_{1-6}$ alkylsulfonyl, methylsulfonyl, ethylsulfonyl and the like are given.

Whereas, as an example for the di-$C_{1-6}$ alkoxymethyl represented by $R^3$, dimethoxymethyl, diethoxymethyl, dipropoxymethyl, diisopropoxymethy 1, dibutoxymethyl, di-t-butoxymethyl and the like are given; and as an example for the di-$C_{1-6}$ alkylthiomethyl, dimethylthiomethyl, diethylthiomethyl, dipropylthiomethyl, diisopropylthiomethyl, dibutylthiomethyl, di-t-butylthiomethyl and the like are given.

Further, as an example for the $C_{1-6}$ alkyl represented by $R^4$ and $R^5$, methyl, ethyl, propyl, isopropyl, butyl, s-butyl, t-butyl and the like are given; as an example for the $C_{1-6}$ haloalkyl, fluoromethyl, 1-fluoroethyl, 2-fluoroethyl, difluoromethyl, trifluoromethyl, difluorochloromethyl, fluorochloromethyl, trichloromethyl, tribromomethyl, trifluoroethyl, pentafluoroethyl and the like are given; as an example for the $C_{2-6}$ alkenyl, vinyl, 1-propenyl, allyl, crotyl, butadienyl and the like are given; as an example for the $C_{2-6}$ alkynyl, ethynyl, 1-propynyl, 2-propynyl, and the like are given; and as an example for the $C_{3-8}$ cycloalkyl, cyclopropyl, cyclopentyl, cyclohexyl and the like are given.

In the compounds according to the present invention and intermediate compounds therefor as described hereunder, carbon atom numbers being contained in substituents are in a range of either from 1 to 6 ($C_{1-6}$) or 2 to 6 ($C_{2-6}$), and preferably either from 1 to 4 ($C_{1-4}$) or 2 to 4 ($C_{2-4}$). The same is applied to the following description.

The compounds according to the present invention can be manufactured pursuant to the following manufacturing method.

Manufacturing Method (i)

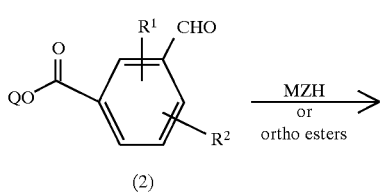

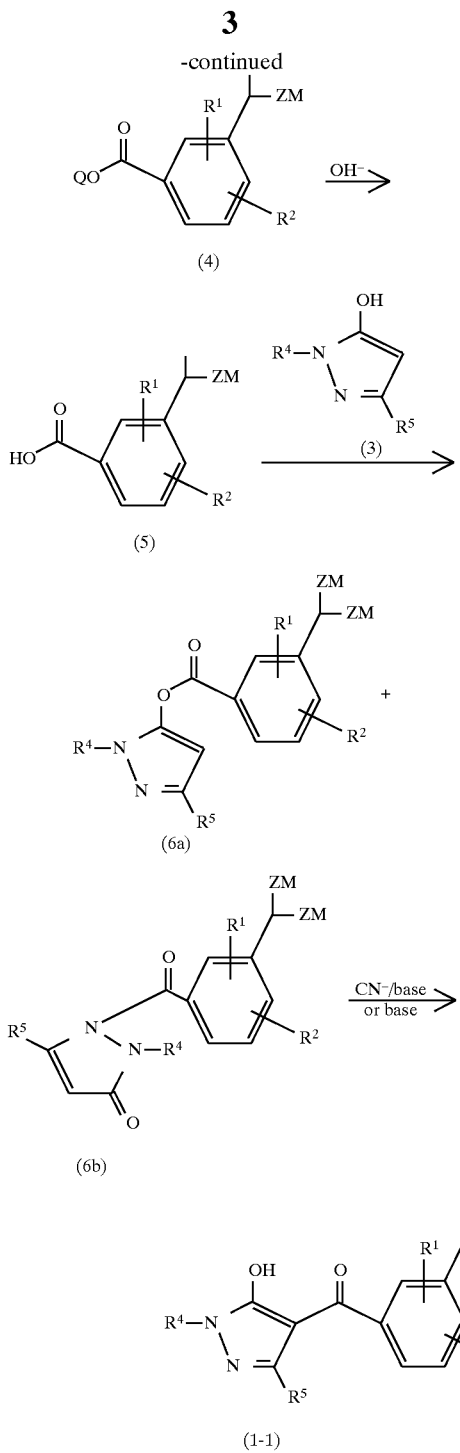

In the manufacturing method described above, $R^1$, $R^2$, $R^4$ and $R^5$ are as defined above, Q is a lower alkyl, Z is oxygen or sulphur, and M is a lower alkyl.

As indicated in the reaction formula described above, a compound of formula (6a) and/or a compound of formula (6b) are manufactured by firstly converting 3-formyl benzoate ester of formula (2) to an acetal compound of formula (4) to obtain a compound of formula (5), then subjecting the compound of formula (5) to a reaction with hydroxypyrazole of formula (3). Consequently, the objective compound of formula (1—1) can be manufactured from the compound of formula (6a) and/or the compound of formula (6b) via a rearrangement reaction.

The compound of formula (4) can be manufactured by proceeding a reaction of the compound of formula (2) in an amount of 1 mol with any of an alcohol, such as methanol and ethanol, an ortho-ester, such as methyl orthoformate, and a mercaptan, such as methyl mercaptan and ethyl mercaptan, in an amount of 1 mol, or an excessive amount can be used for either of the compounds to be used for the reaction, according to a customary method for chemical synthesis, such as a method described in Org. Synth., III, 644 (1955).

The compound of formula (5) can be manufactured from the compound of formula (4) by using an alkali, such as sodium hydroxide, according to a customary method for chemical synthesis.

The compounds of formulas (6a) and (6b) can be obtained by subjecting the compound of formula (5) and the compound of formula (3) to a reaction in the presence of a dehydrating and condensing agent, such as dicyclohexylcarbodiimide (DCC). As an example for a solvent to be used in the reaction with DCC or the like, methylene chloride, chloroform, toluene, ethyl acetate, N,N-dimethylformamide (DMF), tetrahydrofuran (THF), 1,2-dimethoxy ethane, acetonitrile, t-amyl alcohol and the like are given. The mixture prepared for the reaction is stirred at a temperature range of from −10° C. to a boiling point of a solvent used, and the reacted-product is further treated according to a customary method for after-treatment.

The compound of formula (6a) and the compound of formula (6b) are usable as a mixture for the subsequent rearrangement reaction.

The rearrangement reaction is proceeded in the presence of a cyanide and a mild base. More particularly, The compound of formula (1—1) can be obtained by reacting a mixture of the compounds of formula (6a) and (6b) in an amount of 1 mol with a base in an amount of from 1 to 4 mol, preferably from 1 to 2 mol, and a cyanide in an amount of from 0.01 to 1.0 mol, preferably from 0.05 to 0.2 mol.

As an example for the base used in the reaction as described above, an alkali metal hydroxide, such as KOH and NaOH, an alkali metal carbonate, such as sodium carbonate and potassium carbonate, an alkaline earth metal hydroxide, such as calcium hydroxide and magnesium hydroxide, an alkaline earth metal carbonate, such as calcium carbonate, a tertiary amine, such as triethylamine and diisopropyl ethylamine, an organic base, such as pyridine and sodium phosphate, and the like are given.

Also, as an example for the cyanide used as described above, potassium cyanide, sodium cyanide, acetone cyanohydrin, hydrogen cyanide, a polymer holding potassium cyanide and the like are given. It is preferable to add a small amount of a phase-transfer catalyst, such as crown ether, to complete a reaction in a shorter time. It is also preferable to proceed the reaction at a temperature lower than 80° C., and more preferably in a range of from an ambient temperature to 40° C. A solvent usable in the reaction are toluene, acetonitrile, 1,2-dichloro ethane, methylene chloride, chloroform, ethyl acetate, DMF, methyl isobutyl ketone, THF and dimethoxy ethane, for example.

Alternatively, the said rearrangement reaction is accomplished in an inactive solvent and in the presence of a base, such as potassium carbonate, sodium carbonate, triethylamine and pyridine. The amount of the base is in a range of from 0.5 to 2.0 mol based on the total amount of the compounds of formulas (6a) and (6b), and any of THF, dioxane, t-amyl alcohol, t-butyl alcohol and the like can be used as the solvent. Temperature suitable for the reaction is in a range of from an ambient temperature to a boiling point of the solvent used.

Moreover, by using a base together with a dehydrating and condensating agent, such as DCC, and without isolating the compounds of formulas (6a) and (6b), the compound of formula (1—1) can be obtained as well. As an example for the base used in this reaction, potassium carbonate, sodium carbonate, triethylamine, pyridine, etc. are given, and the amount of such base is in a range of from 0.5 to 2.0 mol based on the amount of the compound of formula (3). In this case, any of THF, dioxane, t-amyl alcohol, t-butyl alcohol and the like can be used as the solvent, and it is preferable to proceed the reaction in a temperature range of from an ambient temperature to a boiling point of the solvent used.

Whereas, the compound of formula (4) can be also manufactured according to the following reaction formula which is described in Chem. Ind. (London), 65 (1960), etc.

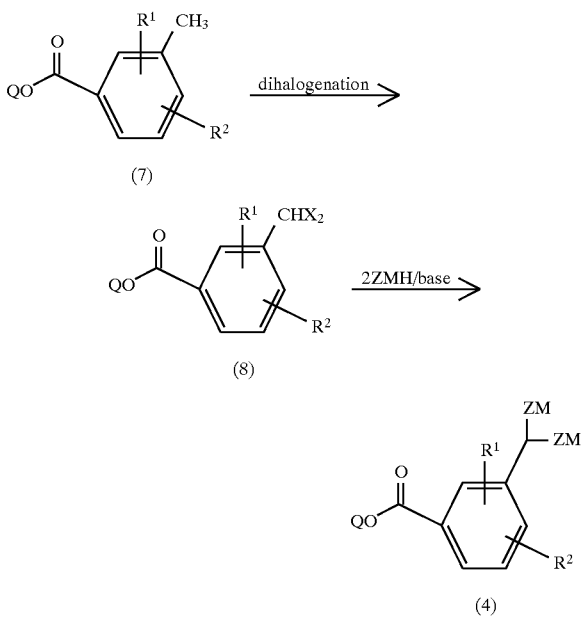

In the reaction formula shown above, $R^1$, $R^2$, Q, Z and M are as defined above, and X is a halogen atom.

In this reaction, the compound of formula (4) is obtained by firstly reacting a toluene derivative of formula (7) with a halogenating agent to obtain a gem-dihalogenated compound of formula (8), then subsequently subjecting it to a reaction with either an alcohol or a mercapto compound, which are represented by a formula, MZH, wherein M and Z are as defined above, in the presence of an appropriate base.

Manufacturing Method (ii)

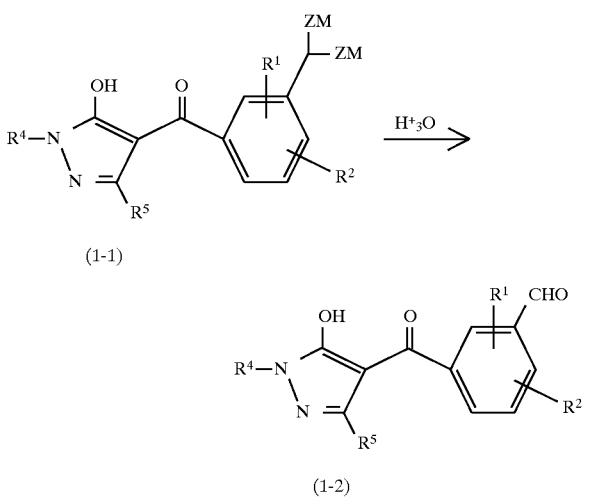

In the reaction formula shown above, $R^1$, $R^2$, $R^4$, $R^5$, Z and M are as defined above.

As shown in the reaction formula above, an objective compound of formula (1–2) is manufactured by causing hydrolysis of an acetal compound of formula (1) with an acid.

In the reaction described above, as such acid used therein, an inorganic acid, such as hydrochloric acid and sulfuric acid, a Louis acid, such as zinc chloride, titan tetrachloride and p-toluenesulfonic acid, an organic acid, such as acetic acid and trifluoroacetic acid, can be given as the examples.

And, as an example for a solvent to be used in this reaction, $H_2O$, an alcohol, such as methanol and ethanol, a halogenated hydrocarbon, such as methylene chloride and chloroform, an aromatic hydrocarbon, such as benzene and toluene, a ketone, such as acetone and methyl ethyl ketone, an ether, such as diethyl ether and THF, acetonitrile, DMF and the like are given.

The mixture prepared for the reaction is stirred at a temperature ranging from $-10°$ C. to a boiling point of a solvent used, and the product obtained from the reaction must be handled according to a customary method for after-treatment.

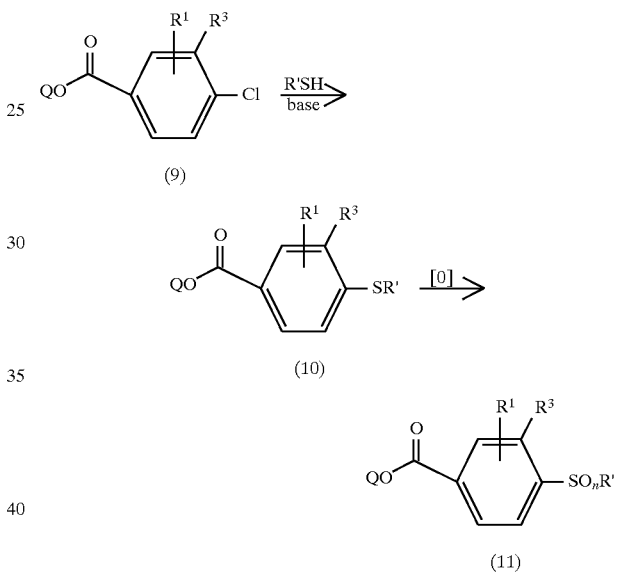

In the reaction formula hereinabove, $R^1$, $R^3$ and Q are as defined above, and R' is a lower alkyl.

A benzoate of formula (11) can be manufactured by firstly subjecting a compound substituted with a chlorine atom at 4th position of its benzene ring of formula (9) with a mercapto compound of formula "R'SH", wherein R' is a lower alkyl, in the presence of a base to obtain a compound substituted with SR' at the 4th-position of its benzene ring of formula (10), then oxidizing the compound of formula (10). The compound of formula (10), wherein $SO_nR'$, wherein n is 1 or 2, is substituted to a position other than the 4th-position of its benzene ring can be obtained by converting from a compound being substituted with a chlorine atom at the corresponding position.

As an example for the base usable in the reaction described hereinabove, an alkali metal hydroxide, such as sodium hydroxide and potassium hydroxide, a metal alkoxide, such as sodium methoxide, sodium ethoxide and potassium t-butoxide, a carbonate, such as sodium carbonate and potassium carbonate, a hydride, such as sodium hydride, an organic base, such as triethylamine, 1,8-diaza-bicyclo[5,4,0]unde-7-cene (DBU) and pyridine, are given. Also, as an example for the solvent used in the reaction, an alcohol, such as methanol and ethanol, an ether, such as THF and 1,2-dimethoxy ethane, an amide, such as DMF and N,N- dimethylacetamide, dimethyl sulfoxide (DMSO), acetonitrile, benzene, toluene, xylene, and the like are given.

The subsequent oxidation reaction is carried out by using an oxidizing agent, for example, a peroxy acid, such as hydrogen peroxide, peracetic acid, perbenzoic acid and m-chloroperbenzoic acid, and a hypochlorous acid, such as sodium hypochloride and potassium hypochloride in an inert solvent, such as water, an organic acid like acetic acid, an alcohol such as methanol or ethanol, a halogenated hydrocarbon like methylene chloride, chloroform or methylene tetrachloride. The reaction may proceed smoothly at a temperature range of from an ambient temperature to a boiling point of a solvent used.

An aldehyde compound of formula (c) shown below, which is an important intermediate for synthesizing the compound according to the present invention, can be manufactured pursuant to the following reaction formula.

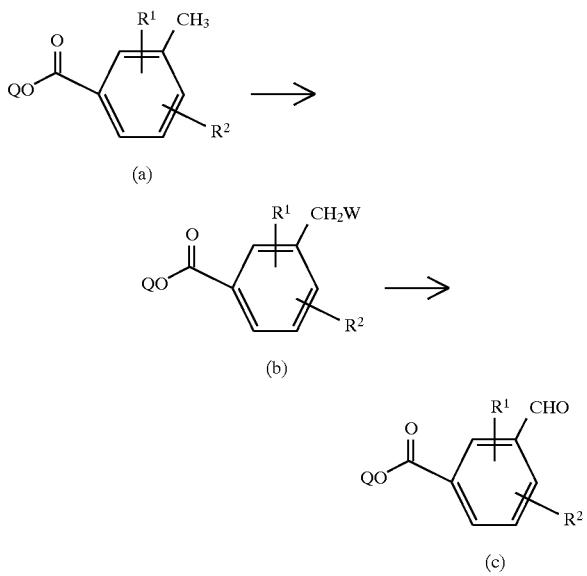

In the reaction formula shown above, $R^1$, $R^2$ and Q are as defined above, and W is a halogen atom.

As can be seen from the reaction formula as shown above, the aldehyde derivative of formula (c) can be manufactured by firstly obtaining a benzylhalide derivative of formula (b) from a toluene derivative of formula (a) according to a publicly-known method, for example, a method to proceed a reaction with either of a halogen atom, such as chlorine and bromine, or a halogenating agent, such as N-bromosuccineimide (NBS) and N-chlorosuccineimide (NCS), in the presence of either light or an initiating agent for radical reaction, such as benzoyl peroxide, then converting the benzylhalide derivative obtained to the aldehyde derivative according to a method described in J. Am. Chem. Soc., 71, 1767 (1949). More particularly, the aldehyde derivative can be manufactured by subjecting the benzylhalide derivative of formula (b) to a reaction with an alkali metal salt of a nitroalkane, such as 2-nitropropane, in an alcohol, such as methanol and ethanol, at a temperature in a range of from 0° C. to a boiling point of a solvent used.

5-hydroxypyrazoles of formula (3) can be manufactured according to the reaction formula represented hereinbelow, which is disclosed in, for examples, Japanese Patent Laid-opens No. Sho 62-234069 Gazette or No. Hei 3-44375 Gazette.

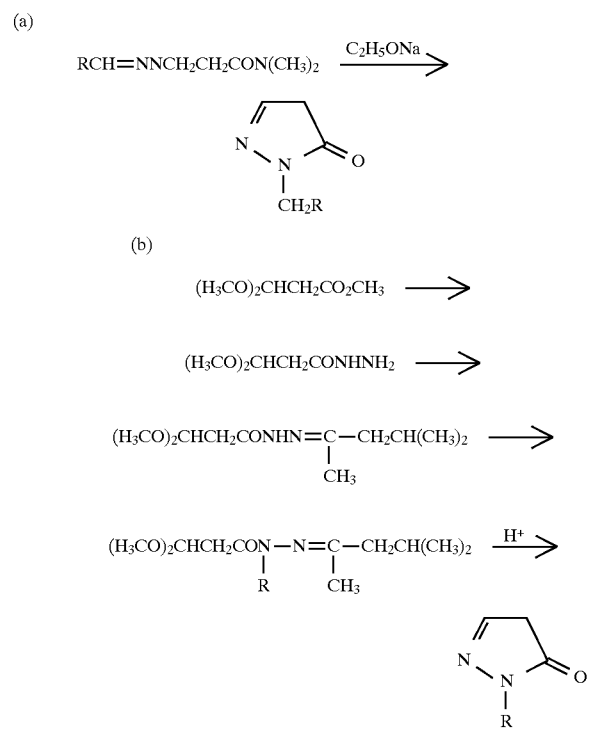

The compound of formula (1) according to the present invention may exist in various forms of tautomers, such like as illustrated below. All of these tautomers shall be included in the scope of the compounds according to the present invention.

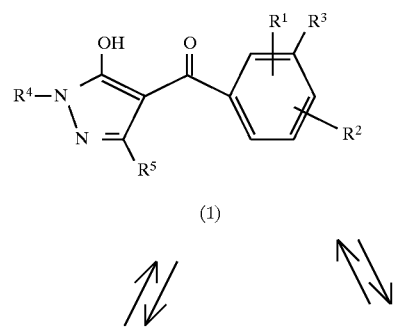

-continued

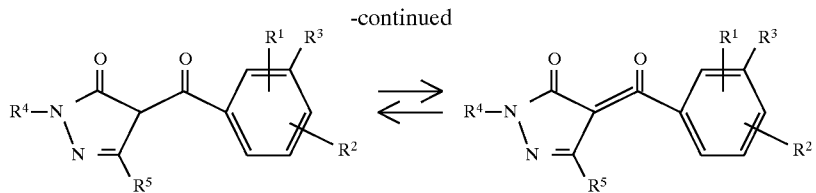

When the compound of formula (1) contains a free hydroxyl group, it is possible to obtain the derivatives from the compound of formula (1), such as the salts thereof, particularly the agriculturally and horticulturally acceptable salts thereof, enamines or those analogs, acylate, sulfonate, carbamate, ether, thioether, sulfoxide and sulfone. As a proper example for the said agriculturally and horticulturally acceptable salts, a sodium salt, a potassium salt, a calcium salt and a ammonium salt are given.

As an example for the ammonium salt, a salt formed with an ion of formula; $N^+RaRbRcRd$, wherein Ra, Rb, Rc and Rd are each independently hydrogen or occasionally a $C_{1-10}$ alkyl substituted by hydroxyl or the like, is given. If any one of Ra, Rb, Rc and Rd is a substituted-alkyl group, it is preferable that Ra, Rb, Rc and Rd contain 1–4 carbon atoms, respectively.

Each of the enamines and those analogs described above are a compound of which part of hydroxy group being converted to a group of formula; —NReRf, wherein Re and Rf are each independently hydrogen, an unsubstituted or substituted $C_{1-6}$ alkyl or an unsubstituted or substituted aryl, such as phenyl, a halogen atom, a group of formula; S(O) gRh, wherein Rh is an unsubstituted or substituted $C_{1-6}$ alkyl or an unsubstituted or substituted aryl, such as phenyl, and g is 0 or an integer of 1 or 2.

Each of the appropriate acylate, an ether and a carbamate derivative described above, is a compound of which part of hydrogen group being converted to a group of formulas; —OCORi, —ORj or —OCONRkRl, wherein Ri and Rj are same as Rh as described above, and Rk and Rl are same as Re as described above.

These derivatives described above can be manufactured according to a customary manufacturing method.

After completing a reaction according to such manufacturing method, it is necessary to take an ordinary after-treatment procedure to obtain the compound of the present invention. The structural formulas of the compounds of the present invention were determined based on examinations conducted by using IR, NMR, MS, etc.

(Herbicide)

The compounds according to the present invention have an excellent herbicidal activity against weeds grown in upland crop fields either by soil application or foliar application method. In particular, the compounds of the present invention can demonstrate higher herbicidal effect on various weeds growing in upland crops, such as giant fox-tails, wild oats, a velvet leaf and pigweed, and some compounds which are selectively non-hazardous to maize, cereals, soybean, cotton, etc. are also contained in such compounds of the present invention.

In the compounds of the present invention, compounds which have plant growth regulating activity, such as growth retarding activity, against useful plants, such as agricultural crops, ornamental plants and fruit trees, are contained as well.

Further, in the compounds of the present invention, compounds which have an excellent herbicidal activity against weeds grown in paddy rice fields, such as barnyardgrass, *Cyperus difformis, Sagittaria trifolia*, and *Scirpus juncoides*, and are selectively non-hazardous to rice plants, are also contained.

In addition, the compounds of the present invention can also be applied for weed control in orchards, lawns, railways, vacant lands, etc.

Moreover, in the compounds of the present invention, compounds which have plant growth regulating activity, fungicidal activity, insecticidal activity and acaricidal activity, are also contained.

The herbicides according to the present invention comprise one or more compounds of the present invention as the active ingredient(s). At a practical application of the compounds of the present invention, such compounds can be applied as it is without combining with other elements. Alternatively, the compounds of the present invention can be prepared into a formulation which is normally employed for plant protection chemicals, such as wettable powder, dust, emulsifiable concentrate, suspension and flowable formulation. As an additive or a filler to be used for a solid-type formulation, vegetable-origin powder, such as soybean powder and wheat flour, mineral fine powder, such as diatomaceous earth, apatite, gypsum, talc, bentonite, pyrophyllite and clay, and organic or inorganic materials, such as sodium benzoate, urea and Glauber's salt, can be used. In case liquid-type formulations are required, a petroleum fraction, such as kerosine, xylene and solvent naphtha, cyclohexane, cyclohexanone, DMF, DMSO alcohol, acetone, trichloroethylene, methylisobutyl ketone, mineral oil, vegetable oil, water, etc. can be used as a solvent. In order to assure uniform and stable physico-chemical properties of such formulations, a surface active agent may be used, if appropriate. As an example for the surface active agent, though there is no particular limitation on that, a non-ionic surface active agent, such as an alkylphenyl ether added with polyoxy ethylene, an alkyl ether added with polyoxy ethylene, a higher fatty acid ester added with polyoxy ethylene, a sorbitan higher fatty acid ester added with polyoxy ethylene and a tristyrylphenyl ether added with polyoxy ethylene; a sulfate ester and an alkylbenzenesulfonate of an alkylphenyl ether added with polyoxy ethylene; a sulfate ester, an alkyl sulfate, an alkylnaphthalenesulfonate, a polycarboxylate and a ligninsulfonate of a higher alcohol, a formaldehyde condensate of an alkyl naphthalene sulfonate, an isobutylene-anhydrous maleic acid co-polymer and the like are given.

The content of an active ingredient in the herbicide according to the present invention may differ depending upon formulation types as described above. For example, the content of the active ingredient can be in a range of from 5 to 90% by weight (hereinafter %), and preferably from 10 to 85%, for a wettable powder formulation; from 3 to 70%, and preferably from 5 to 60%, for an emulsifiable concentrate formulation; and from 0.01 to 50%, and preferably from 0.05 to 40%, for a granular formulation.

The wettable powder and the emulsifiable concentrate obtained as described above can be applied in a form of suspension or emulsion, respectively, after diluting them with appropriate volume of water. The granules obtained as described above can be directly applied to and/or incorporated into soil without dilution prior to or after germination of weeds. At a practical application of the herbicide according to the present invention, an active ingredient in an appropriate amount more than 0.1 g/ha shall be applied.

The herbicide according to the present invention can be used in mixing with any of other known fungicides, insecticides, acaricides, herbicides, plant growth regulators, fertilizers, etc. In particular, it is possible to reduce a required dose of the inventive herbicide to use thanks to a mixing with other herbicides. In this case, such mixing may provide an effect not only to reduce labours required for weeding but also to give higher herbicidal performance because of a synergistic action derived from a herbicide mixed together. Mixing of the inventive herbicide with a plurality of other known herbicides is also allowable.

As an example for a herbicide to be preferably associated with the inventive herbicide, an anilide herbicide, such as diflufenican and propanil, a chloroacetoanilide herbicide, such as alachlor and pretilachlor, an aryloxy alkanoic acid herbicide, such as 2,4-D and 2,4-DB, an aryloxyphenoxy-alkanic acid herbicides, such as diclofopmethyl and phenoxaprop-ethyl, an arylcarboxylic acid herbicide, such as dicamba, pyrithiobac, an imidazolinone herbicide, such as imazaquin and imazethapyr, an urea herbicide, such as diuron and isoproturon, a carbamate herbicide, such as chlorprofam and phenmediphame, a thiocarbamate herbicide, such as thiobencarb and EPTC, a dinitro aniline herbicide, such as trifluraline and pendimethalin, a diphenyl ether herbicide, such as acifluorfen and fomesafen, a sulfonylurea herbicide, such as bensulfuron-methyl and nicosulfuron, a triazinone herbicide, such as metribuzin and metamitron, a triazine herbicide, such as atrazine and cyanazine, a triazopyrimidine herbicide, such as flumeturam, a nitrile-type herbicide, such as bromoxynil and dichlobenil, a phosphoric acid herbicide, such as glyphosate and glyphosinate, a quaternized ammonium salt herbicide, such as paraquat and difenzoquat, a cyclic imide herbicide, such as flumiclorac-pentyl and fluthiacet-methyl, isoxaben, ethofumesate, quinclorac, cromazone, sulcotrione, synmethyline, dithiopyr, pyrazolate, pyridate, flupoxam, bentazon, benflusate, and a cyclohexanedione herbicides, such as sethoxydim and tralcoxydim, are given. In addition, a vegetable oil and an oil concentrate may be added to a mixture of the inventive herbicide with one or more of the herbicides exemplified above.

BEST MODE FOR CARRYING OUT THE INVENTION

Now, the present invention is further described in detail with referring to the following Examples and Reference Examples.

EXAMPLE 1

Preparation of 1-ethyl-5-hydroxy-4-(2-chloro-4-methanesulfonyl-3-dimethoxymethylbenzoyl) pyrazole (Compound No. 1–2)

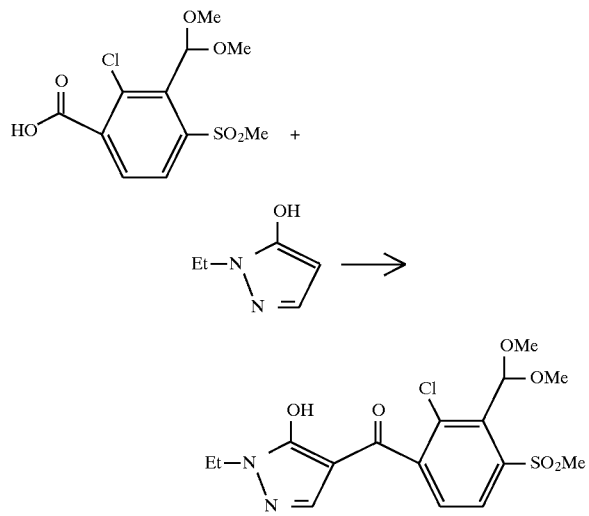

To ethyl acetate in a volume of 50 ml, was dissolved 2-chloro-4-methanesulfonyl-3-dimethoxymethylbenzoic acid in an amount of 3.0 g (9.7 mmol), and to the resulting solution, were added DCC in an amount of 2.2 g (10.7 mmol) and 1-ethyl-5-hydroxypyrazole hydrochloride in an amount of 1.4 g (9.7 mmol) while cooling with ice and the mixture was subsequently stirred for a night at an ambient temperature. Insoluble product precipitated was filtrated, and the filtrate was condensed under reduce pressure. The residue obtained was then dissolved in chloroform in a volume of 30 ml, and the resulting solution was stirred for 6 hours at an ambient temperature following to an addition of acetone cyanohydrin in an amount of 0.25 g (2.9 mmol) and triethylamine in an amount of 2.0 g (20 mmol) thereto. The reacted-mixture was washed with 1-N hydrochloric acid and then with saturated saline solution, dried over anhydrous magnesium sulfate and subjected to distillation for eliminating the solvent therein. The crystals remained were washed with methanol to obtain 1-ethyl-5-hydroxy-4-(2-chloro-4-methanesulfonyl-3-dimethoxymethylbenzoyl) pyrazole in an amount of 1.6 g. The melting point of this compound is in a range of from 168° to 170° C.

EXAMPLE 2

Preparation of 1-methyl-5-hydroxy-4-(2-chloro-4-methanesulfonyl-3-dimethylthiomethylbenzoyl) pyrazole (Compound No. 1–6)

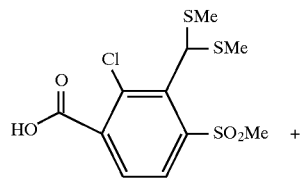

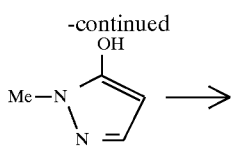

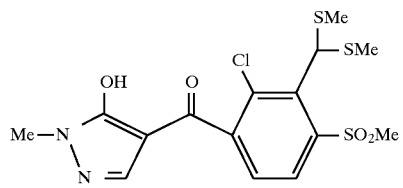

To ethyl acetate in a volume of 20 ml, was dissolved 2-chloro-4-methanesulfonyl-3-dimethylthiobenzoic acid in an amount of 0.84 g (2.5 mmol), and to the resulting solution, were added DCC in an amount of 0.56 g (2.8 mmol), 1-methyl-5-hydroxypyrazole hydrochloride in an amount of 0.33 g (2.5 mmol) and triethylamine in an amount of 0.25 g (2.5 g (2. 5 mmol) while cooling with ice and the mixture was subsequently stirred for a night at an ambient temperature. Insoluble product precipitated was filtrated, and the filtrate was condensed under reduce pressure. The residue obtained was then dissolved in chloroform in a volume of 10 ml, and the resulting solution was stirred for a night at an ambient temperature following to an addition of acetone cyanohydrin in an amount of 0.06 g (0.7 mmol) and triethylamine in an amount of 0.5 g (5 mmol) thereto. The reacted-mixture was washed with 1-N hydrochloric acid and then with saturated saline solution, dried over anhydrous magnesium sulfate and subjected to distillation for eliminating the solvent therein. The crystals remained were washed with methanol to obtain 1-methyl-5-hydroxy-4-(2-chloro-4-methanesulfonyl-3-dimethylthiomethylbenzoyl)pyrazole in an amount of 0.26 g. The melting point of this compound is in a range of from 215° to 217° C.

EXAMPLE 3

Preparation of 1-methyl-5-hydroxy-4-(2-chloro-4-methanesulfonyl-3-formylbenzoyl)pyrazole (Compound No. 2–1)

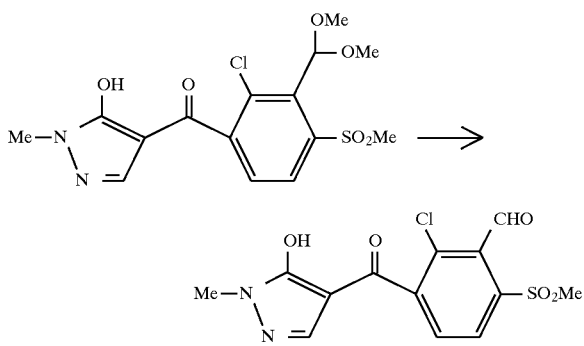

To acetone in a volume of 40 ml, was dissolved 1-methyl-5-hydroxy-4-(2-chloro-4-methanesulfonyl-3-dimethoxymethylbenzoyl)pyrazole in an amount of 1.8 g (4.7 mmol), and hydrochloric acid in an amount of 2 ml was then added to the resulting solution. The mixture was stirred for 1 hour under heating reflux, and the solvent therein was removed by distillation. Crystals precipitated was washed with ether to obtain 1-methyl-5-hydroxy-4-(2-chloro-4-methanesulfonyl-3-formylbenzoyl)pyrazole in an amount of 1.5 g. The melting point of this compound is in a range of from 140° to 142° C.

Now, examples for preparing intermediates which are important for the compounds according to the present invention are described hereinbelow as reference.

Reference Example 1

Preparation of methyl 2,4-dichloro-3-formyl benzoate

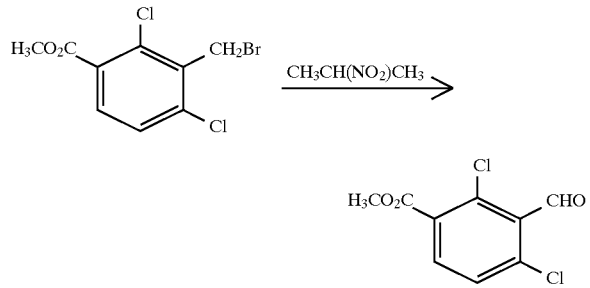

To methanol in a volume of 100 ml, was added 28% methanol solution of sodium methylate in an amount of 26.61 g, and to the resulting solution, was fed dropwise 2-nitro propane in an amount of 12.29 g while cooling with ice to a temperature lower than 25° C. The mixture was then added with methyl 3-bromomethyl-2,4-dichlorobenzoate in an amount of 41.16 g and stirred for 30 minutes under heating reflux. After completing reaction, the reacted-mixture was cooled and condensed under reduced pressure. A residue obtained was then dissolved in ethyl acetate in a volume of 1,000 ml, and the resulting solution was then washed with 1% aqueous solution of sodium hydroxide while cooling with ice. An organic layer resulted was washed with water and then with saturated saline solution, and was dried over anhydrous magnesium sulfate. Crystals, which were obtained after condensation of the organic layer under reduce pressure, were washed with benzene and then with n-hexane to obtain an objective compound of methyl 2,4-dichloro-3-formylbenzoate in an amount of 22.0 g in crystalline state. The melting point of this compound is in a range of from 103° to 104° C.

Reference Example 2

Preparation of 2,4-dichloro-3-formylbenzoic acid

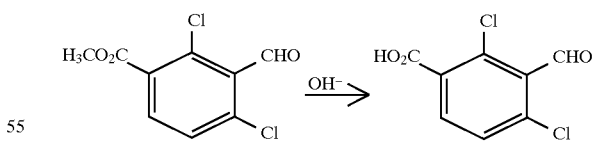

Methyl 2,4-dichloro-3-formyl benzoate in an amount of 1.04 g was dissolved in ethanol in an amount of 5 ml, and the resulting solution was then added with 1-N solution of sodium hydroxide in an amount of 10 ml and subsequently stirred for 17 hours at an ambient temperature. The reacted-solution was then poured into ice water in a volume of 40 ml, and the mixture was adjusted with concentrated sulfuric acid to acidic condition. Crystals precipitated were filtrated and dried to obtain an objective compound of 2,4-dichloro-3-formylbenzoic acid in an amount of 0.75 g in crystalline

Reference Example 3

Preparation of methyl 2-chloro-4-methanesulfonyl-3-dimethoxymethyl benzoate

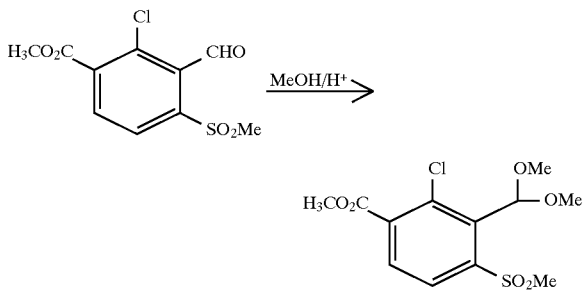

Methyl 2-chloro-4-methanesulfonyl-3-formyl benzoate in an amount of 3.0 g (11 mmol) was dissolved in methanol in a volume of 50 ml, and the resulting solution was then added with concentrated sulfuric acid in an amount of 0.5 g and subsequently stirred for 8 hours under heating reflux. After condensing solvent in the mixture under reduced pressure, a residue obtained was dissolved in benzene, washed with 3% aqueous solution of sodium hydrogencarbonate and then with saturated saline solution and further dried over anhydrous magnesium sulfate. After condensing the solvent and then purifying the condensate with silica gel column chromatography for obtaining the objective compound in an amount of 3.0 g.

$^1$H-NMR ($\delta$ppm, CDCL$_3$): 3.24(3H, s), 3.54(6H, s), 3.98 (3H, s), 6.28(1H, s), 7.70(1H, d), 8.19(1H, d)

Reference Example 4

Preparation of 2-chloro-4-methanesulfonyl-3-dimethoxymethylbenzoic acid

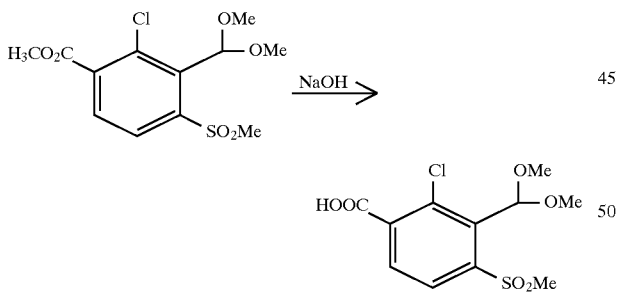

Methyl 2-chloro-4-methanesulfonyl-3-dimethoxymethylbenzoate in an amount of 3.0 g (9.3 mmol) was dissolved in methanol in a volume of 30 ml, and to the resulting solution, was added 10% aqueous solution of sodium hydroxide in a volume of 20 ml, and then, the mixture was stirred for 1 hour at an ambient temperature. The reacted-mixture was then added with 1-N hydrochloric acid to make it acidic, and crystals precipitated were filtrated, washed with water and dried to obtain the objective compound in an amount of 2.5 g.

$^1$H-NMR($\delta$ppm, CDCl$_3$): 2.99(3H, s), 3.56(6H, s), 6.29 (1H, s), 7.89(1H, d), 8.24(1H, d)

Reference Example 5

Preparation of methyl 2-chloro-4-methanesulfonyl-3-dimethylthiomethylbenzoate

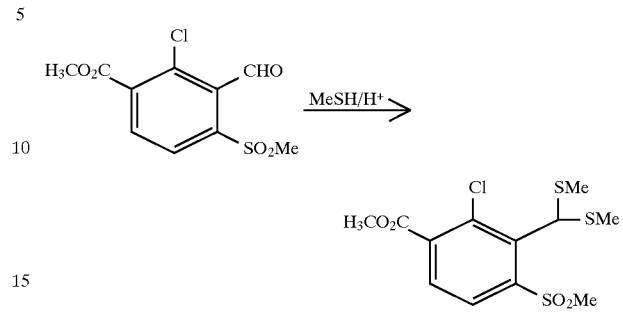

Methyl 2-chloro-4-methanesulfonyl-3-formylbenzoate in an amount of 1.5 g (5.4 mmol) was dissolved in methylene chloride in a volume of 15 ml, and to the resulting solution, methylmercaptan in an amount of 0.65 g (14 mmol) was gradually blown under a temperature of 10° C. Then, aluminium chloride in an amount of 0.22 g (1.7 mmol) was gradually added to the mixture at 10° C. and was stirred for 3 hours at an ambient temperature. The reacted-mixture was washed with water and dried over anhydrous magnesium sulfate, and following to condensating solvent therein under reduced pressure, the objective compound in an amount of 1.8 g was obtained.

$^1$H-NMR($\delta$ppm, CDCl$_3$): 2.37(6H, s), 3.24(3H, s), 3.98 (3H, s), 6.22(1H, s), 7.66(1H, d). 8.10(1H, d)

Reference Example 6

Preparation of 2-chloro-4-methanesulfonyl-3-dimethylthiomethylbenzoic acid

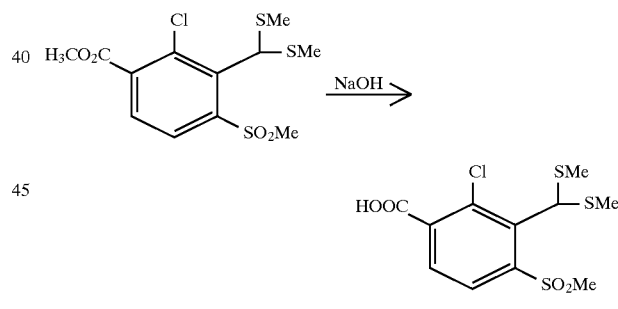

Methyl 2-chloro-4-methanesulfonyl-3-dimethlthiomethylbenzoate in an amount of 1.80 g (5.08 mmol) was dissolved in methanol in a volume of 10 ml, and to the resulting solution, was added 10% aqueous solution of sodium hydroxide in a volume of 10 ml, and then, the mixture was stirred for 8 hour at an ambient temperature. The reacted-mixture was then added with 1-N hydrochloric acid to make it acidic, and crystals precipitated were filtrated, washed with water and dried to obtain the objective compound in an amount of 1.69 g.

$^1$H-NMR($\delta$ppm, CDCl$_3$): 2.33(6H, s), 3. 22(3H, s), 6.21 (1H, s), 7.68(1H, d), 8.04(1H, d)

Now, the representative examples for the compounds according to the present invention including the compounds prepared in the examples described above are represented in Tables 1 and 2.

state. The melting point of this compound is in a range of from 188° to 190° C.

TABLE 1

| Compound No. | R¹ | R² | R⁴ | R⁵ | ZM | Physical Data [ ] Melting Point °C. |
|---|---|---|---|---|---|---|
| 1-1 | 2-Cl | 4-SO$_2$Me | Me | H | OMe | [157–159] |
| 1-2 | 2-Cl | 4-SO$_2$Me | Et | H | OMe | [168–170] |
| 1-3 | 2-Cl | 4-SO$_2$Me | Me | Me | OMe | [235–237] |
| 1-4 | 2-Cl | 4-SO$_2$Me | Me | H | OEt | amorphous NMR-1 |
| 1-5 | 2-Cl | 4-SO$_2$Me | Et | H | OEt | amorphous NMR-2 |
| 1-6 | 2-Cl | 4-SO$_2$Me | Me | H | SMe | [215–217] |
| 1-7 | 2-Cl | 4-SO$_2$Me | Et | H | SMe | [183–185] |
| 1-8 | 2-CH$_3$ | 4-SO$_2$Me | Me | H | OMe | [164–167] |
| 1-9 | 2-CH$_3$ | 4-SO$_2$Me | Et | H | OMe | [148–150] |
| 1-10 | 2-Cl | 4-SO$_2$Me | Me | Me | SMe | |
| 1-11 | 2-Cl | 4-SO$_2$Me | Me | Et | OMe | |
| 1-12 | 2-Cl | 4-SO$_2$Me | Me | Et | SMe | |
| 1-13 | 2-Cl | 4-SO$_2$Me | Me | CH=CH$_2$ | OMe | |
| 1-14 | 2-Cl | 4-SO$_2$Me | Me | CH$_2$CH=CH$_2$ | OMe | |
| 1-15 | 2-Cl | 4-SO$_2$Me | Me | C≡CH | OMe | |
| 1-16 | 2-Cl | 4-SO$_2$Me | Me | CH$_2$C≡CH | OMe | |
| 1-17 | 2-Cl | 4-SO$_2$Me | Me | cyclopropyl | OMe | |
| 1-18 | 2-Cl | 4-SO$_2$Me | Me | cyclohexyl | OMe | |
| 1-19 | 2-Cl | 4-SO$_2$Me | Me | CF$_3$ | OMe | |
| 1-20 | 2-Cl | 4-SO$_2$Me | Me | CH=CH$_2$ | SMe | |
| 1-21 | 2-Cl | 4-SO$_2$Me | Me | CH$_2$CH=CH$_2$ | SMe | |
| 1-22 | 2-Cl | 4-SO$_2$Me | Me | C≡CH | SMe | |
| 1-23 | 2-Cl | 4-SO$_2$Me | Me | CH$_2$C≡CH | SMe | |
| 1-24 | 2-Cl | 4-SO$_2$Me | Me | cyclopropyl | SMe | |
| 1-25 | 2-Cl | 4-SO$_2$Me | Me | cyclohexyl | SMe | |
| 1-26 | 2-Cl | 4-SO$_2$Me | Me | CF$_3$ | SMe | |
| 1-27 | 2-Cl | 4-Cl | Me | CH=CH$_2$ | OMe | |
| 1-28 | 2-Cl | 4-Cl | Me | CH$_2$CH=CH$_2$ | OMe | |
| 1-29 | 2-Cl | 4-Cl | Me | C≡CH | OMe | |
| 1-30 | 2-Cl | 4-Cl | Me | CH$_2$C≡CH | OMe | |
| 1-31 | 2-Cl | 4-Cl | Me | cyclopropyl | OMe | |
| 1-32 | 2-Cl | 4-Cl | Me | cyclohexyl | OMe | |
| 1-33 | 2-Cl | 4-Cl | Me | CF$_3$ | OMe | |
| 1-34 | 2-Cl | 4-Cl | Me | CH$_2$CH=CH$_2$ | SMe | |
| 1-35 | 2-Cl | 4-Cl | Me | CH$_2$C≡CH | SMe | |
| 1-36 | 2-Cl | 4-Cl | Me | cyclopropyl | SMe | |
| 1-37 | 2-Cl | 4-Cl | Me | CF$_3$ | SMe | |
| 1-38 | 2-Me | 4-SO$_2$Me | Me | Me | OMe | |
| 1-39 | 2-Me | 4-SO$_2$Me | Me | Et | OMe | |
| 1-40 | 2-Me | 4-SO$_2$Me | Me | CH$_2$CH=CH$_2$ | OMe | |
| 1-41 | 2-Me | 4-SO$_2$Me | Me | CH$_2$C≡CH | OMe | |
| 1-42 | 2-Me | 4-SO$_2$Me | Me | cyclopropyl | OMe | |
| 1-43 | 2-Me | 4-SO$_2$Me | Me | CF$_3$ | OMe | |
| 1-44 | 2-Me | 4-SO$_2$Me | Me | Me | SMe | |
| 1-45 | 2-Me | 4-SO$_2$Me | Me | Et | SMe | |
| 1-46 | 2-Me | 4-SO$_2$Me | Me | CH$_2$CH=CH$_2$ | SMe | |
| 1-47 | 2-Me | 4-SO$_2$Me | Me | CH$_2$C≡CH | SMe | |
| 1-48 | 2-Me | 4-SO$_2$Me | Me | cyclopropyl | SMe | |
| 1-49 | 2-Me | 4-SO$_2$Me | Me | CF$_3$ | SMe | |
| 1-50 | 2-CF$_3$ | 4-SO$_2$Me | Me | H | OMe | |
| 1-51 | 2-CF$_3$ | 4-SO$_2$Me | Me | Me | OMe | |
| 1-52 | 2-CF$_3$ | 4-SO$_2$Me | Me | CH$_2$CH=CH$_2$ | OMe | |
| 1-53 | 2-CF$_3$ | 4-SO$_2$Me | Me | CH$_2$C≡CH | OMe | |
| 1-54 | 2-CF$_3$ | 4-SO$_2$Me | Me | cyclopropyl | OMe | |
| 1-55 | 2-CF$_3$ | 4-SO$_2$Me | Me | CF$_3$ | OMe | |
| 1-56 | 2-CF$_3$ | 4-SO$_2$Me | Me | H | SMe | |

TABLE 1-continued

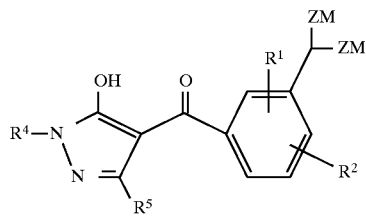

| Compound No. | $R^1$ | $R^2$ | $R^4$ | $R^5$ | ZM | Physical Data [ ] Melting Point °C. |
|---|---|---|---|---|---|---|
| 1-57 | 2-CF$_3$ | 4-SO$_2$Me | Me | Me | SMe | |
| 1-58 | 2-CF$_3$ | 4-SO$_2$Me | Me | CH$_2$CH=CH$_2$ | SMe | |
| 1-59 | 2-CF$_3$ | 4-SO$_2$Me | Me | CH$_2$C≡CH | SMe | |
| 1-60 | 2-CF$_3$ | 4-SO$_2$Me | Me | cyclopropyl | SMe | |
| 1-61 | 2-CF$_3$ | 4-SO$_2$Me | Me | CF$_3$ | SMe | |
| 1-62 | 2-OMe | 4-SO$_2$Me | Me | H | OMe | |
| 1-63 | 2-OMe | 4-SO$_2$Me | Me | Me | OMe | |
| 1-64 | 2-OMe | 4-SO$_2$Me | Me | CH$_2$CH=CH$_2$ | OMe | |
| 1-65 | 2-OMe | 4-SO$_2$Me | Me | CH$_2$C≡CH | OMe | |
| 1-66 | 2-OMe | 4-SO$_2$Me | Me | cyclopropyl | OMe | |
| 1-67 | 2-OMe | 4-SO$_2$Me | Me | CF$_3$ | OMe | |
| 1-68 | 2-OMe | 4-SO$_2$Me | Me | H | SMe | |
| 1-69 | 2-OMe | 4-SO$_2$Me | Me | Me | SMe | |
| 1-70 | 2-OMe | 4-SO$_2$Me | Me | CH$_2$CH=CH$_2$ | SMe | |
| 1-71 | 2-OMe | 4-SO$_2$Me | Me | CH$_2$C≡CH | SMe | |
| 1-72 | 2-OMe | 4-SO$_2$Me | Me | cyclopropyl | SMe | |
| 1-73 | 2-OMe | 4-SO$_2$Me | Me | CF$_3$ | SMe | |
| 1-74 | 2-OCF$_3$ | 4-SO$_2$Me | Me | H | OMe | |
| 1-75 | 2-OCF$_3$ | 4-SO$_2$Me | Me | Me | OMe | |
| 1-76 | 2-OCF$_3$ | 4-SO$_2$Me | Me | CH$_2$CH=CH$_2$ | OMe | |
| 1-77 | 2-OCF$_3$ | 4-SO$_2$Me | Me | CH$_2$C≡CH | OMe | |
| 1-78 | 2-OCF$_3$ | 4-SO$_2$Me | Me | cyclopropyl | OMe | |
| 1-79 | 2-OCF$_3$ | 4-SO$_2$Me | Me | CF$_3$ | OMe | |
| 1-80 | 2-OCF$_3$ | 4-SO$_2$Me | Me | H | SMe | |
| 1-81 | 2-OCF$_3$ | 4-SO$_2$Me | Me | Me | SMe | |
| 1-82 | 2-OCF$_3$ | 4-SO$_2$Me | Me | CH$_2$CH=CH$_2$ | SMe | |
| 1-83 | 2-OCF$_3$ | 4-SO$_2$Me | Me | CH$_2$C≡CH | SMe | |
| 1-84 | 2-OCF$_3$ | 4-SO$_2$Me | Me | cyclopropyl | SMe | |
| 1-85 | 2-OCF$_3$ | 4-SO$_2$Me | Me | CF$_3$ | SMe | |
| 1-86 | 2-Cl | 4-Cl | Et | CH=CH$_2$ | OMe | |
| 1-87 | 2-Cl | 4-Cl | Et | CH$_2$CH=CH$_2$ | OMe | |
| 1-88 | 2-Cl | 4-Cl | Et | C≡CH | OMe | |
| 1-89 | 2-Cl | 4-Cl | Et | CH$_2$C≡CH | OMe | |
| 1-90 | 2-Cl | 4-Cl | Et | cyclopropyl | OMe | |
| 1-91 | 2-Cl | 4-Cl | Et | cyclohexyl | OMe | |
| 1-92 | 2-Cl | 4-Cl | Et | CF$_3$ | OMe | |
| 1-93 | 2-Cl | 4-Cl | Et | CH$_2$CH=CH$_2$ | SMe | |
| 1-94 | 2-Cl | 4-Cl | Et | CH$_2$C≡CH | SMe | |
| 1-95 | 2-Cl | 4-Cl | Et | cyclopropyl | SMe | |
| 1-96 | 2-Cl | 4-Cl | Et | CF$_3$ | SMe | |
| 1-97 | 2-Me | 4-SO$_2$Me | Et | Me | OMe | |
| 1-98 | 2-Me | 4-SO$_2$Me | Et | Et | OMe | |
| 1-99 | 2-Me | 4-SO$_2$Me | Et | CH$_2$CH=CH$_2$ | OMe | |
| 1-100 | 2-Me | 4-SO$_2$Me | Et | CH$_2$C≡CH | OMe | |
| 1-101 | 2-Me | 4-SO$_2$Me | Et | cyclopropyl | OMe | |
| 1-102 | 2-Me | 4-SO$_2$Me | Et | CF$_3$ | OMe | |
| 1-103 | 2-Me | 4-SO$_2$Me | Et | Me | SMe | |
| 1-104 | 2-Me | 4-SO$_2$Me | Et | Et | SMe | |
| 1-105 | 2-Me | 4-SO$_2$Me | Et | CH$_2$CH=CH$_2$ | SMe | |
| 1-106 | 2-Me | 4-SO$_2$Me | Et | CH$_2$C≡CH | SMe | |
| 1-107 | 2-Me | 4-SO$_2$Me | Et | cyclopropyl | SMe | |
| 1-108 | 2-Me | 4-SO$_2$Me | Et | CF$_3$ | SMe | |
| 1-109 | 2-CF$_3$ | 4-SO$_2$Me | Et | H | OMe | |
| 1-110 | 2-CF$_3$ | 4-SO$_2$Me | Et | Me | OMe | |
| 1-111 | 2-CF$_3$ | 4-SO$_2$Me | Et | CH$_2$CH=CH$_2$ | OMe | |

TABLE 1-continued

[Structure: pyrazole with OH, R⁴-N, R⁵, connected via C=O to benzene ring with R¹, R², and CH(ZM)(ZM) group]

| Compound No. | R¹ | R² | R⁴ | R⁵ | ZM | Physical Data [ ] Melting Point °C. |
|---|---|---|---|---|---|---|
| 1-112 | 2-CF₃ | 4-SO₂Me | Et | CH₂C≡CH | OMe | |
| 1-113 | 2-CF₃ | 4-SO₂Me | Et | cyclopropyl | OMe | |
| 1-114 | 2-CF₃ | 4-SO₂Me | Et | CF₃ | OMe | |
| 1-115 | 2-CF₃ | 4-SO₂Me | Et | H | SMe | |
| 1-116 | 2-CF₃ | 4-SO₂Me | Et | Me | SMe | |
| 1-117 | 2-CF₃ | 4-SO₂Me | Et | CH₂CH=CH₂ | SMe | |
| 1-118 | 2-CF₃ | 4-SO₂Me | Et | CH₂C≡CH | SMe | |
| 1-119 | 2-CF₃ | 4-SO₂Me | Et | cyclopropyl | SMe | |
| 1-120 | 2-CF₃ | 4-SO₂Me | Et | CF₃ | SMe | |
| 1-121 | 2-OMe | 4-SO₂Me | Et | H | OMe | |
| 1-122 | 2-OMe | 4-SO₂Me | Et | Me | OMe | |
| 1-123 | 2-OMe | 4-SO₂Me | Et | CH₂CH=CH₂ | OMe | |
| 1-124 | 2-OMe | 4-SO₂Me | Et | CH₂C≡CH | OMe | |
| 1-125 | 2-OMe | 4-SO₂Me | Et | cyclopropyl | OMe | |
| 1-126 | 2-OMe | 4-SO₂Me | Et | CF₃ | OMe | |
| 1-127 | 2-OMe | 4-SO₂Me | Et | H | SMe | |
| 1-128 | 2-OMe | 4-SO₂Me | Et | Me | SMe | |
| 1-129 | 2-OMe | 4-SO₂Me | Et | CH₂CH=CH₂ | SMe | |
| 1-130 | 2-OMe | 4-SO₂Me | Et | CH₂C≡CH | SMe | |
| 1-131 | 2-OMe | 4-SO₂Me | Et | cyclopropyl | SMe | |
| 1-132 | 2-OMe | 4-SO₂Me | Et | CF₃ | SMe | |
| 1-133 | 2-OCF₃ | 4-SO₂Me | Et | H | OMe | |
| 1-134 | 2-OCF₃ | 4-SO₂Me | Et | Me | OMe | |
| 1-135 | 2-OCF₃ | 4-SO₂Me | Et | CH₂CH=CH₂ | OMe | |
| 1-136 | 2-OCF₃ | 4-SO₂Me | Et | CH₂C≡CH | OMe | |
| 1-137 | 2-OCF₃ | 4-SO₂Me | Et | cyclopropyl | OMe | |
| 1-138 | 2-OCF₃ | 4-SO₂Me | Et | CF₃ | OMe | |
| 1-139 | 2-OCF₃ | 4-SO₂Me | Et | H | SMe | |
| 1-140 | 2-OCF₃ | 4-SO₂Me | Et | Me | SMe | |
| 1-141 | 2-OCF₃ | 4-SO₂Me | Et | CH₂CH=CH₂ | SMe | |
| 1-142 | 2-OCF₃ | 4-SO₂Me | Et | CH₂C≡CH | SMe | |
| 1-143 | 2-OCF₃ | 4-SO₂Me | Et | cyclopropyl | SMe | |
| 1-144 | 2-OCF₃ | 4-SO₂Me | Et | CF₃ | SMe | |
| 1-145 | 2-Cl | 4-SMe | Me | H | OMe | |
| 1-146 | 2-Cl | 4-SMe | Et | H | OMe | |
| 1-147 | 2-Cl | 4-SMe | Me | Me | SMe | |
| 1-148 | 2-Cl | 4-SMe | Et | Me | SMe | |
| 1-149 | 2-Cl | 4-SOMe | Me | H | OMe | |
| 1-150 | 2-Cl | 4-SOMe | Et | H | OMe | |
| 1-151 | 2-Cl | 4-SOMe | Me | Me | SMe | |
| 1-152 | 2-Cl | 4-SOMe | Et | Me | SMe | |
| 1-153 | 2-F | 4-SO₂Me | Me | H | OMe | |
| 1-154 | 2-F | 4-SO₂Me | Et | H | OMe | |
| 1-155 | 2-F | 4-SO₂Me | Me | Me | SMe | |
| 1-156 | 2-F | 4-SO₂Me | Et | Me | SMe | |
| 1-157 | 2-Br | 4-SO₂Me | Me | H | OMe | |
| 1-158 | 2-Br | 4-SO₂Me | Et | H | OMe | |
| 1-159 | 2-Br | 4-SO₂Me | Me | Me | SMe | |
| 1-160 | 2-Br | 4-SO₂Me | Et | Me | SMe | |
| 1-161 | 2-Cl | 4-SO₂Me | H | H | OMe | |
| 1-162 | 2-Cl | 4-SO₂Me | H | H | SMe | |
| 1-163 | 2-Cl | 4-SO₂Me | H | Me | OMe | |
| 1-164 | 2-SO₂Me | 4-Cl | H | H | OMe | |
| 1-165 | 2-SO₂Me | 4-Cl | Me | H | OMe | |
| 1-166 | 2-SO₂Me | 4-Cl | CH₂CH=CH₂ | H | OMe | |
| 1-167 | 2-SO₂Me | 4-Cl | CH₂C≡CH | H | OMe | |
| 1-168 | 2-SO₂Me | 4-Cl | cyclopropyl | H | OMe | |
| 1-169 | 2-SO₂Me | 4-Cl | CF₃ | H | OMe | |
| 1-170 | 2-SO₂Me | 4-Me | H | H | OMe | |

TABLE 1-continued

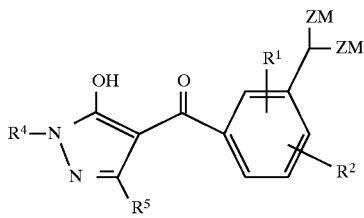

| Compound No. | $R^1$ | $R^2$ | $R^4$ | $R^5$ | ZM | Physical Data [ ] Melting Point °C. |
|---|---|---|---|---|---|---|
| 1-171 | 2-SO$_2$Me | 4-Me | Me | H | OMe | |
| 1-172 | 2-SO$_2$Me | 4-Me | CH$_2$CH=CH$_2$ | H | OMe | |
| 1-173 | 2-SO$_2$Me | 4-Me | CH$_2$C≡CH | H | OMe | |
| 1-174 | 2-SO$_2$Me | 4-Me | cyclopropyl | H | OMe | |
| 1-175 | 2-SO$_2$Me | 4-Me | CF$_3$ | H | OMe | |
| 1-176 | 2-SO$_2$Me | 4-CF$_3$ | Me | H | OMe | |
| 1-177 | 2-SO$_2$Me | 4-CF$_3$ | CH$_2$CH=CH$_2$ | H | OMe | |
| 1-178 | 2-SO$_2$Me | 4-CF$_3$ | CH$_2$C≡CH | H | OMe | |
| 1-179 | 2-SO$_2$Me | 4-CF$_3$ | cyclopropyl | H | OMe | |
| 1-180 | 2-SO$_2$Me | 4-CF$_3$ | CF$_3$ | H | OMe | |
| 1-181 | 2-SO$_2$Me | 4-OMe | Me | H | OMe | |
| 1-182 | 2-SO$_2$Me | 4-OMe | CH$_2$CH=CH$_2$ | H | OMe | |
| 1-183 | 2-SO$_2$Me | 4-OMe | CH$_2$C≡CH | H | OMe | |
| 1-184 | 2-SO$_2$Me | 4-OMe | cyclopropyl | H | OMe | |
| 1-185 | 2-SO$_2$Me | 4-OMe | CF$_3$ | H | OMe | |
| 1-186 | 2-SO$_2$Me | 4-OCF$_3$ | Me | H | OMe | |
| 1-187 | 2-SO$_2$Me | 4-OCF$_3$ | CH$_2$CH=CH$_2$ | H | OMe | |
| 1-188 | 2-SO$_2$Me | 4-OCF$_3$ | CH$_2$C≡CH | H | OMe | |
| 1-189 | 2-SO$_2$Me | 4-OCF$_3$ | cyclopropyl | H | OMe | |
| 1-190 | 2-SO$_2$Me | 4-OCF$_3$ | CF$_3$ | H | OMe | |
| 1-191 | 2-SMe | 4-Cl | Et | H | OMe | |
| 1-192 | 2-SOMe | 4-Cl | Et | H | OMe | |
| 1-193 | 2-Cl | 5-SO$_2$Me | Me | H | OMe | |
| 1-194 | 2-Cl | 6-SO$_2$Me | Me | H | OMe | |
| 1-195 | 4-Cl | 5-SO$_2$Me | Me | H | OMe | |
| 1-196 | 4-Cl | 6-SO$_2$Me | Me | H | OMe | |
| 1-197 | 2-Cl | 4-SO$_2$Me | Me | H | OEt | |
| 1-198 | 2-Cl | 4-SO$_2$Me | Me | H | SEt | |
| 1-199 | 2-Cl | 4-SO$_2$Me | Me | H | OPr$^i$ | |
| 1-200 | 2-Cl | 4-SO$_2$Me | Me | H | SPr$^i$ | |
| 1-201 | 2-Cl | 4-SO$_2$Me | Me | H | OBu | |
| 1-202 | 2-Cl | 4-SO$_2$Me | Me | H | SBu | |
| 1-203 | 2-NO$_2$ | 4-Cl | Me | H | OMe | |
| 1-204 | 2-NO$_2$ | 4-Cl | CH$_2$CH=CH$_2$ | H | OMe | |
| 1-205 | 2-NO$_2$ | 4-Cl | CH$_2$C≡CH | H | OMe | |
| 1-206 | 2-NO$_2$ | 4-Cl | cyclopropyl | H | OMe | |
| 1-207 | 2-NO$_2$ | 4-Cl | CF$_3$ | H | OMe | |
| 1-208 | 2-NO$_2$ | 2-SO$_2$Me | Me | H | OMe | |
| 1-209 | 2-NO$_2$ | 2-SO$_2$Me | CH$_2$CH=CH$_2$ | H | OMe | |
| 1-210 | 2-NO$_2$ | 2-SO$_2$Me | CH$_2$C≡CH | H | OMe | |
| 1-211 | 2-NO$_2$ | 2-SO$_2$Me | cyclopropyl | H | OMe | |
| 1-212 | 2-NO$_2$ | 2-SO$_2$Me | CF$_3$ | H | OMe | |
| 1-213 | 2-NO$_2$ | 4-Cl | Me | H | SMe | |
| 1-214 | 2-NO$_2$ | 4-Cl | CH$_2$CH=CH$_2$ | H | SMe | |
| 1-215 | 2-NO$_2$ | 4-Cl | CH$_2$C≡CH | H | SMe | |
| 1-216 | 2-NO$_2$ | 4-Cl | cyclopropyl | H | SMe | |
| 1-217 | 2-NO$_2$ | 4-Cl | CF$_3$ | H | SMe | |
| 1-218 | 2-NO$_2$ | 2-SO$_2$Me | Me | H | SMe | |
| 1-219 | 2-NO$_2$ | 2-SO$_2$Me | CH$_2$CH=CH$_2$ | H | SMe | |
| 1-220 | 2-NO$_2$ | 2-SO$_2$Me | CH$_2$C≡CH | H | SMe | |
| 1-221 | 2-NO$_2$ | 2-SO$_2$Me | cyclopropyl | H | SMe | |
| 1-222 | 2-NO$_2$ | 2-SO$_2$Me | CF$_3$ | H | SMe | |
| 1-228 | 2-Cl | 4-SO$_2$Me | $^i$Pr | H | SMe | |
| 1-229 | 2-Cl | 4-SO$_2$Me | Bu | H | SMe | |
| 1-230 | 2-Cl | 4-SO$_2$Me | $^i$Pr | H | SMe | |
| 1-231 | 2-Cl | 4-SO$_2$Me | Bu | H | SMe | |
| 1-232 | 2-CN | 4-Cl | Me | H | OMe | |
| 1-233 | 2-CN | 4-Cl | CH$_2$CH=CH$_2$ | H | OMe | |

TABLE 1-continued

[Structure: R⁴—N-N=C(R⁵)—C(=O)—(pyrazole with OH)—C(=O)—phenyl(R¹, R², CH(ZM)₂)]

| Compound No. | R¹ | R² | R⁴ | R⁵ | ZM | Physical Data [ ] Melting Point °C. |
|---|---|---|---|---|---|---|
| 1-234 | 2-CN | 4-Cl | CH₂C≡CH | H | OMe | |
| 1-235 | 2-CN | 4-Cl | cyclopropyl | H | OMe | |
| 1-236 | 2-CN | 4-Cl | CF₃ | H | OMe | |
| 1-237 | 2-CN | 2-SO₂Me | Me | H | OMe | |
| 1-238 | 2-CN | 2-SO₂Me | CH₂CH=CH₂ | H | OMe | |
| 1-239 | 2-CN | 2-SO₂Me | CH₂C≡CH | H | OMe | |
| 1-240 | 2-CN | 2-SO₂Me | cyclopropyl | H | OMe | |
| 1-241 | 2-CN | 2-SO₂Me | CF₃ | H | OMe | |
| 1-242 | 2-CN | 4-CF₃ | Me | H | OMe | |
| 1-243 | 2-CN | 4-CF₃ | CH₂CH=CH₂ | H | OMe | |
| 1-244 | 2-CN | 4-CF₃ | CH₂C≡CH | H | OMe | |
| 1-245 | 2-CN | 4-CF₃ | cyclopropyl | H | OMe | |
| 1-246 | 2-CN | 4-CF₃ | CF₃ | H | OMe | |
| 1-247 | 2-CF₃ | 4-CN | Me | H | OMe | |
| 1-248 | 2-CF₃ | 4-CN | CH₂CH=CH₂ | H | OMe | |
| 1-249 | 2-CF₃ | 4-CN | CH₂C≡CH | H | OMe | |
| 1-250 | 2-CF₃ | 2-CN | cyclopropyl | H | OMe | |
| 1-251 | 2-CF₃ | 2-CN | CF₃ | H | OMe | |
| 1-252 | 2-CN | 4-Cl | Me | H | SMe | |
| 1-253 | 2-CN | 4-Cl | CH₂CH=CH₂ | H | SMe | |
| 1-254 | 2-CN | 4-Cl | CH₂C≡CH | H | SMe | |
| 1-255 | 2-CN | 4-Cl | cyclopropyl | H | SMe | |
| 1-256 | 2-CN | 4-Cl | CF₃ | H | SMe | |
| 1-257 | 2-CN | 2-SO₂Me | Me | H | SMe | |
| 1-258 | 2-CN | 2-SO₂Me | CH₂CH=CH₂ | H | SMe | |
| 1-259 | 2-CN | 2-SO₂Me | CH₂C≡CH | H | SMe | |
| 1-260 | 2-CN | 2-SO₂Me | cyclopropyl | H | SMe | |
| 1-261 | 2-CN | 2-SO₂Me | CF₃ | H | SMe | |
| 1-262 | 2-CN | 4-CF₃ | Me | H | SMe | |
| 1-263 | 2-CN | 4-CF₃ | CH₂CH=CH₂ | H | SMe | |
| 1-264 | 2-CN | 4-CF₃ | CH₂C≡CH | H | SMe | |
| 1-265 | 2-CN | 4-CF₃ | cyclopropyl | H | SMe | |
| 1-266 | 2-CN | 4-CF₃ | CF₃ | H | SMe | |
| 1-267 | 2-CF₃ | 4-CN | Me | H | SMe | |
| 1-268 | 2-CF₃ | 4-CN | CH₂CH=CH₂ | H | SMe | |
| 1-269 | 2-CF₃ | 4-CN | CH₂C≡CH | H | SMe | |
| 1-270 | 2-CF₃ | 4-CN | cyclopropyl | H | SMe | |
| 1-271 | 2-CF₃ | 4-CN | CF₃ | H | SMe | |
| 1-272 | 2-CF₃ | 4-CF₃ | Me | H | OMe | |
| 1-273 | 2-CF₃ | 4-CF₃ | Et | H | OMe | |
| 1-274 | 2-CF₃ | 4-CF₃ | Me | H | SMe | |
| 1-275 | 2-CF₃ | 4-CF₃ | Et | H | SMe | |

TABLE 2

[Structure: pyrazole with R4-N, OH, R5, connected via C=O to phenyl ring with R1, CHO, R2 substituents]

| Compound No. | R$^1$ | R$^2$ | R$^4$ | R$^5$ | Physical Data [ ]Melting Point °C. |
|---|---|---|---|---|---|
| 2-1 | 2-Cl | 4-SO$_2$Me | Me | H | [140–142] |
| 2-2 | 2-Cl | 4-SO$_2$Me | Et | H | [202–204] |
| 2-3 | 2-Cl | 4-SO$_2$Me | Me | Me | [174–178] |
| 2-4 | 2-Cl | 4-SO$_2$Me | Me | H | |
| 2-5 | 2-Cl | 4-SO$_2$Me | Et | H | |
| 2-6 | 2-Cl | 4-SO$_2$Me | Me | CH=CH$_2$ | |
| 2-7 | 2-Cl | 4-SO$_2$Me | Me | CH$_2$CH=CH$_2$ | |
| 2-8 | 2-Cl | 4-SO$_2$Me | Me | C≡CH | |
| 2-9 | 2-Cl | 4-SO$_2$Me | Me | CH$_2$C≡CH | |
| 2-10 | 2-Cl | 4-SO$_2$Me | Me | cyclopropyl | |
| 2-11 | 2-Cl | 4-SO$_2$Me | Me | cyclohexyl | |
| 2-12 | 2-Cl | 4-SO$_2$Me | Me | CF$_3$ | |
| 2-13 | 2-Cl | 4-Cl | Me | H | |
| 2-14 | 2-Cl | 4-Cl | Me | Me | |
| 2-15 | 2-Cl | 4-Cl | Me | CH=CH$_2$ | |
| 2-16 | 2-Cl | 4-Cl | Me | CH$_2$CH=CH$_2$ | |
| 2-17 | 2-Cl | 4-Cl | Me | C≡CH | |
| 2-18 | 2-Cl | 4-Cl | Me | CH$_2$C≡CH | |
| 2-19 | 2-Cl | 4-Cl | Me | cyclopropyl | |
| 2-20 | 2-Cl | 4-Cl | Me | cyclohexyl | |
| 2-21 | 2-Cl | 4-Cl | Me | CF$_3$ | |
| 2-22 | 2-Me | 4-SO$_2$Me | Me | H | [185–187] |
| 2-23 | 2-Me | 4-SO$_2$Me | Me | CH=CH$_2$ | |
| 2-24 | 2-Me | 4-SO$_2$Me | Me | CH$_2$CH=CH$_2$ | |
| 2-25 | 2-Me | 4-SO$_2$Me | Me | C≡CH | |
| 2-26 | 2-Me | 4-SO$_2$Me | Me | CH$_2$C≡CH | |
| 2-27 | 2-Me | 4-SO$_2$Me | Me | cyclopropyl | |
| 2-28 | 2-Me | 4-SO$_2$Me | Me | cyclohexyl | |
| 2-29 | 2-Me | 4-SO$_2$Me | Me | CF$_3$ | |
| 2-30 | 2-CF$_3$ | 4-SO$_2$Me | Me | H | |
| 2-31 | 2-CF$_3$ | 4-SO$_2$Me | Me | Me | |
| 2-32 | 2-CF$_3$ | 4-SO$_2$Me | Me | CH$_2$CH=CH$_2$ | |
| 2-33 | 2-CF$_3$ | 4-SO$_2$Me | Me | CH$_2$C≡CH | |
| 2-34 | 2-CF$_3$ | 4-SO$_2$Me | Me | cyclopropyl | |
| 2-35 | 2-CF$_3$ | 4-SO$_2$Me | Me | CF$_3$ | |
| 2-36 | 2-OMe | 4-SO$_2$Me | Me | H | |
| 2-37 | 2-OMe | 4-SO$_2$Me | Me | Me | |
| 2-38 | 2-OMe | 4-SO$_2$Me | Me | CH$_2$CH=CH$_2$ | |
| 2-39 | 2-OMe | 4-SO$_2$Me | Me | CH$_2$C≡CH | |
| 2-40 | 2-OMe | 4-SO$_2$Me | Me | cyclopropyl | |
| 2-41 | 2-OMe | 4-SO$_2$Me | Me | CF$_3$ | |
| 2-42 | 2-OCF$_3$ | 4-SO$_2$Me | Me | H | |
| 2-43 | 2-OCF$_3$ | 4-SO$_2$Me | Me | Me | |
| 2-44 | 2-OCF$_3$ | 4-SO$_2$Me | Me | CH$_2$CH=CH$_2$ | |
| 2-45 | 2-OCF$_3$ | 4-SO$_2$Me | Me | CH$_2$C≡CH | |
| 2-46 | 2-OCF$_3$ | 4-SO$_2$Me | Me | cyclopropyl | |
| 2-47 | 2-OCF$_3$ | 4-SO$_2$Me | Me | CF$_3$ | |
| 2-48 | 2-Cl | 4-SO$_2$Me | Et | CH=CH$_2$ | |
| 2-49 | 2-Cl | 4-SO$_2$Me | Et | CH$_2$CH=CH$_2$ | |
| 2-50 | 2-Cl | 4-SO$_2$Me | Et | C≡CH | |
| 2-51 | 2-Cl | 4-SO$_2$Me | Et | CH$_2$C≡CH | |
| 2-52 | 2-Cl | 4-SO$_2$Me | Et | cyclopropyl | |
| 2-53 | 2-Cl | 4-SO$_2$Me | Et | cyclohexyl | |
| 2-54 | 2-Cl | 4-SO$_2$Me | Et | CF$_3$ | |
| 2-55 | 2-Cl | 4-Cl | Et | H | |
| 2-56 | 2-Cl | 4-Cl | Et | Me | |
| 2-57 | 2-Cl | 4-Cl | Et | CH=CH$_2$ | |

TABLE 2-continued

| Compound No. | R¹ | R² | R⁴ | R⁵ | Physical Data [ ]Melting Point °C. |
|---|---|---|---|---|---|
| 2-58 | 2-Cl | 4-Cl | Et | CH₂CH=CH₂ | |
| 2-59 | 2-Cl | 4-Cl | Et | C≡CH | |
| 2-60 | 2-Cl | 4-Cl | Et | CH₂C≡CH | |
| 2-61 | 2-Cl | 4-Cl | Et | cyclopropyl | |
| 2-62 | 2-Cl | 4-Cl | Et | cyclohexyl | |
| 2-63 | 2-Cl | 4-Cl | Et | CF₃ | |
| 2-64 | 2-Me | 4-SO₂Me | Et | H | [211–213] |
| 2-65 | 2-Me | 4-SO₂Me | Et | CH=CH₂ | |
| 2-66 | 2-Me | 4-SO₂Me | Et | CH₂CH=CH₂ | |
| 2-67 | 2-Me | 4-SO₂Me | Et | C≡CH | |
| 2-68 | 2-Me | 4-SO₂Me | Et | CH₂C≡CH | |
| 2-69 | 2-Me | 4-SO₂Me | Et | cyclopropyl | |
| 2-70 | 2-Me | 4-SO₂Me | Et | cyclohexyl | |
| 2-71 | 2-Me | 4-SO₂Me | Et | CF₃ | |
| 2-72 | 2-CF₃ | 4-SO₂Me | Et | H | |
| 2-73 | 2-CF₃ | 4-SO₂Me | Et | Me | |
| 2-74 | 2-CF₃ | 4-SO₂Me | Et | CH₂CH=CH₂ | |
| 2-75 | 2-CF₃ | 4-SO₂Me | Et | CH₂C≡CH | |
| 2-76 | 2-CF₃ | 4-SO₂Me | Et | cyclopropyl | |
| 2-77 | 2-CF₃ | 4-SO₂Me | Et | CF₃ | |
| 2-78 | 2-OMe | 4-SO₂Me | Et | H | |
| 2-79 | 2-OMe | 4-SO₂Me | Et | Me | |
| 2-80 | 2-OMe | 4-SO₂Me | Et | CH₂CH=CH₂ | |
| 2-81 | 2-OMe | 4-SO₂Me | Et | CH₂C≡CH | |
| 2-82 | 2-OMe | 4-SO₂Me | Et | cyclopropyl | |
| 2-83 | 2-OMe | 4-SO₂Me | Et | CF₃ | |
| 2-84 | 2-OCF₃ | 4-SO₂Me | Et | H | |
| 2-85 | 2-OCF₃ | 4-SO₂Me | Et | Me | |
| 2-86 | 2-OCF₃ | 4-SO₂Me | Et | CH₂CH=CH₂ | |
| 2-87 | 2-OCF₃ | 4-SO₂Me | Et | CH₂C≡CH | |
| 2-88 | 2-OCF₃ | 4-SO₂Me | Et | cyclopropyl | |
| 2-89 | 2-OCF₃ | 4-SO₂Me | Et | CF₃ | |
| 2-90 | 2-Cl | 4-SMe | Me | H | |
| 2-91 | 2-Cl | 4-SMe | Et | H | |
| 2-92 | 2-Cl | 4-SMe | Me | Me | |
| 2-93 | 2-Cl | 4-SMe | Et | Me | |
| 2-94 | 2-Cl | 4-SOMe | Me | H | |
| 2-95 | 2-Cl | 4-SOMe | Et | H | |
| 2-96 | 2-Cl | 4-SOMe | Me | Me | |
| 2-97 | 2-Cl | 4-SOMe | Et | Me | |
| 2-98 | 2-F | 4-SO₂Me | Me | H | |
| 2-99 | 2-F | 4-SO₂Me | Et | H | |
| 2-100 | 2-F | 4-SO₂Me | Me | Me | |
| 2-101 | 2-F | 4-SO₂Me | Et | Me | |
| 2-102 | 2-Br | 4-SO₂Me | Me | H | |
| 2-103 | 2-Br | 4-SO₂Me | Et | H | |
| 2-104 | 2-Br | 4-SO₂Me | Me | Me | |
| 2-105 | 2-Br | 4-SO₂Me | Et | Me | |
| 2-106 | 2-Cl | 4-SO₂Et | Me | H | |
| 2-107 | 2-Cl | 4-SO₂Et | Et | H | |
| 2-108 | 2-Cl | 4-SO₂Et | Me | Me | |
| 2-109 | 2-Cl | 4-SO₂Et | Et | Me | |
| 2-110 | 2-SO₂Me | 4-Cl | H | H | |
| 2-111 | 2-SO₂Me | 4-Cl | Me | H | |
| 2-112 | 2-SO₂Me | 4-Cl | Et | H | |
| 2-113 | 2-SO₂Me | 4-Cl | CH₂CH=CH₂ | H | |
| 2-114 | 2-SO₂Me | 4-Cl | CH₂C≡CH | H | |
| 2-115 | 2-SO₂Me | 4-Cl | cyclopropyl | H | |
| 2-116 | 2-SO₂Me | 4-Cl | CF₃ | H | |
| 2-117 | 2-SO₂Me | 4-Me | Me | H | |

TABLE 2-continued

Structure: pyrazole with R4-N, OH, connected via C=O to phenyl ring with R1, CHO, R2; R5 on pyrazole.

| Compound No. | R¹ | R² | R⁴ | R⁵ | Physical Data [ ]Melting Point °C. |
|---|---|---|---|---|---|
| 2-118 | 2-SO₂Me | 4-Me | Et | H | |
| 2-119 | 2-SO₂Me | 4-Me | CH₂CH=CH₂ | H | |
| 2-120 | 2-SO₂Me | 4-Me | CH₂C≡CH | H | |
| 2-121 | 2-SO₂Me | 4-Me | cyclopropyl | H | |
| 2-122 | 2-SO₂Me | 4-Me | CF₃ | H | |
| 2-123 | 2-SO₂Me | 4-CF₃ | Me | H | |
| 2-124 | 2-SO₂Me | 4-CF₃ | Et | H | |
| 2-125 | 2-SO₂Me | 4-CF₃ | CH₂CH=CH₂ | H | |
| 2-126 | 2-SO₂Me | 4-CF₃ | CH₂C≡CH | H | |
| 2-127 | 2-SO₂Me | 4-CF₃ | cyclopropyl | H | |
| 2-128 | 2-SO₂Me | 4-CF₃ | CF₃ | H | |
| 2-129 | 2-SO₂Me | 4-OMe | Me | H | |
| 2-130 | 2-SO₂Me | 4-OMe | Et | H | |
| 2-131 | 2-SO₂Me | 4-OMe | CH₂CH=CH₂ | H | |
| 2-132 | 2-SO₂Me | 4-OMe | CH₂C≡CH | H | |
| 2-133 | 2-SO₂Me | 4-OMe | CH₂CH=CH₂ | H | |
| 2-134 | 2-SO₂Me | 4-OMe | CH₂C≡CH | H | |
| 2-135 | 2-SO₂Me | 4-OCF₃ | Me | H | |
| 2-136 | 2-SO₂Me | 4-OCF₃ | Et | H | |
| 2-137 | 2-SO₂Me | 4-OCF₃ | CH₂CH=CH₂ | H | |
| 2-138 | 2-SO₂Me | 4-OCF₃ | CH₂C≡CH | H | |
| 2-139 | 2-SO₂Me | 4-OCF₃ | cyclopropyl | H | |
| 2-140 | 2-SO₂Me | 4-OCF₃ | CF₃ | H | |
| 2-141 | 2-SMe | 4-Cl | Me | H | |
| 2-142 | 2-SMe | 4-Cl | Me | Me | |
| 2-143 | 2-SMe | 4-Cl | Et | H | |
| 2-144 | 2-SOMe | 4-Cl | Me | H | |
| 2-145 | 2-SOMe | 4-Cl | Et | H | |
| 2-146 | 2-NO₂ | 4-Cl | Me | H | |
| 2-147 | 2-NO₂ | 4-Cl | Et | H | |
| 2-148 | 2-NO₂ | 4-SO₂Me | Me | H | |
| 2-149 | 2-NO₂ | 4-SO₂Me | Et | H | |
| 2-150 | 2-Cl | 4-NO₂ | Me | H | |
| 2-151 | 2-Cl | 4-NO₂ | Et | H | |
| 2-152 | 2-Cl | 4-NO₂ | Me | Me | |
| 2-153 | 2-CN | 4-Cl | Me | H | |
| 2-154 | 2-CN | 4-Cl | Et | H | |
| 2-155 | 2-CN | 4-SO₂Me | Me | H | |
| 2-156 | 2-CN | 4-SO₂Me | Et | H | |
| 2-157 | 2-Cl | 4-CN | Me | H | |
| 2-158 | 2-Cl | 4-CN | Et | H | |
| 2-159 | 2-Cl | 4-CN | Et | H | |
| 2-160 | 2-CF₃ | 4-CN | Me | H | |
| 2-161 | 2-CF₃ | 4-CN | Et | H | |
| 2-162 | 2-CF₃ | 4-CN | Me | Me | |
| 2-163 | 2-CN | 4-SO₂Me | CH₂CH=CH₂ | H | |
| 2-164 | 2-CN | 4-SO₂Me | CH₂C≡CH | H | |
| 2-165 | 2-CN | 4-SO₂Me | cyclopropyl | H | |
| 2-166 | 2-CN | 4-SO₂Me | CF₃ | H | |
| 2-167 | 2-CN | 4-CF₃ | Me | H | |
| 2-168 | 2-CN | 4-CF₃ | Et | H | |
| 2-169 | 2-CN | 4-CF₃ | Me | Me | |
| 2-170 | 2-CN | 4-CF₃ | Pr$^i$ | H | |

Hereunder are ¹H-NMR(CDCL₃, δppm from TMS) data for the compounds of the present invention.

NMR-1 (Compound No. 1–4): 1.26(6H, t), 3.28(3H, s), 3.60(2H, m), 3.70(3H, s), 3.86(2H, m), 6.45(1H, s), 7.29 (1H, s), 7.50(1H, d), 8.21(1H, d)

NMR-2 (Compound No. 1–5): 1.27(6H, t), 1.45(3H, t), 3.31(3H, s), 3.63(2H, m), 3.88(2H, m), 4.08(2H, q), 6.47 (1H, s), 7.30(1H, s), 7.51), 8.23(1H, d)

(Herbicide)

Now, some formulation examples suitable to the herbicide according to present invention are given hereinbelow.

However, the active ingredients and, types and additional portions of additives contained in such formulations shall be modified over a wide range and shall not be limited to the ones specified in the examples described below. Parts indicated in the following formulation examples means parts by weight.

EXAMPLE 4
Wettable Powder

| | |
|---|---|
| The inventive compound | 20 parts |
| White carbon | 20 parts |
| Diatomaceous earth | 52 parts |
| Sodium alkylsulfate | 8 parts |

All materials are uniformly mixed and grinded up to fine powders to thereby obtain a wettable powder formulation containing 20% active ingredient.

EXAMPLE 5
Emulsifiable Concentrate

| | |
|---|---|
| The inventive compound | 20 parts |
| Xylene | 55 parts |
| Dimethylformamide | 15 parts |
| Polyoxyethylenephenyl ether | 10 parts |

All materials are mixed and dissolved to obtain an emulsifiable concentrate formulation containing 20% active ingredient.

EXAMPLE 6
Granules

| | |
|---|---|
| The inventive compound | 5 parts |
| Talc | 40 parts |
| Clay | 38 parts |
| Bentonite | 10 parts |
| Sodium alkylsulfate | 7 parts |

All materials are uniformly mixed, grinded up to fine powders and granulated into granules having a diameter of from 0.5 to 1.0 mm to thereby obtain a granular formulation containing 5% active ingredient.

Industrial Use of the Invention

Test examples which are carried out to show a herbicidal activity of the herbicides according to the present invention are now described hereinbelow.

Herbicidal activity is evaluated puruant to the following criterion, and it is expressed as an index for killed-weeds.

| Criterion for assessment | |
|---|---|
| % of Killed-weeds | Index for Killed-weeds |
| 0% | 0 |
| 20–29% | 2 |
| 40–49% | 4 |
| 60–69% | 6 |
| 80–89% | 8 |
| 100% | 10 |

Indexes 1, 3, 5, 7 and 9 represent an intermediate activity between 0 and 2, 2 and 4, 4 and 6, 6 and 8, 8 and 10, respectively.

% of Killed-weed=[(Weight of fresh weeds growing over the ground in non-treated plot−Weight of fresh weeds growing over the ground in a treated-plot)÷(Weight of fresh weeds growing over the ground in non-treated plot)]×100

Test Example 1
Foliar Application

In a 200 cm$^2$ planting pot filled with soil, all seeds of velvet leaf, pigweed, cocklebur, giant foxtail and maize wee planted over its soil surface, and the seeds were covered with slight amount of soil to grow in a greenhouse. When each plants has grown to 5 to 25 cm height, respectively, an emulsion prepared from an emulsifiable concentrate formulation prepared in the example 5 being adjusted at a desired concentration by diluting with water was sprayed to thier shoots at a volume rate of 1000 liters/ha by using a small sprayer. 3 weeks later, herbicidal performance and phytotoxicity on maize were checked, respectively, according to the criterion as described above, showing the results in Table 3.

TABLE 3

| Compound No. | Dose g/ha | Velvet leaf | Pigweed | Cocklebur | Giant foxtail | Maize |
|---|---|---|---|---|---|---|
| 1-1 | 250 | 10 | 10 | 10 | 10 | 9 |
| 1-2 | 250 | 10 | 10 | 10 | 10 | 2 |
| 1-3 | 250 | 8 | 10 | 10 | 10 | 6 |
| 1-4 | 250 | 10 | 10 | 10 | 10 | 8 |
| 1-5 | 250 | 10 | 10 | 10 | 10 | 6 |
| 2-1 | 250 | 8 | 10 | 8 | 10 | 0 |
| 2-2 | 250 | 9 | 10 | 10 | 10 | 0 |
| 2-3 | 250 | 8 | 7 | 9 | 10 | 0 |

What is claimed is:

1. A compound of formula (1);

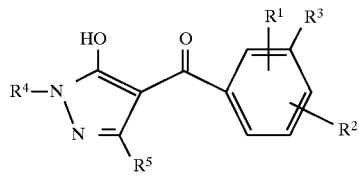

wherein $R^1$, $R^2$ are each independently hydrogen, a halogen atom, nitro, cyano, a $C_{1-6}$ alkyl, a $C_{1-6}$ alkoxy, a $C_{1-6}$ haloalkyl, a $C_{1-6}$ haloalkoxy, a $C_{1-6}$ alkylthio, a $C_{1-6}$ alkylsulfinyl or a $C_{1-6}$ alkylsulfonyl, $R^3$ is formyl, a di-$C_{1-6}$ alkoxymethyl or a $C_{1-6}$ alkylthiomethyl, and $R^4$ and $R^5$ are each independently hydrogen, a $C_{1-6}$ alkyl, a $C_{1-6}$ haloalkyl, a $C_{2-6}$ alkenyl, $C_{2-6}$ alkynyl or a $C_{3-8}$ cycloalkyl, and a salt thereof.

2. A herbicide comprising one or more of compounds of formula (1);

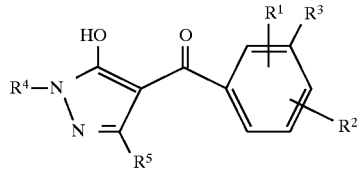

wherein $R^1$, $R^2$, $R^3$, $R^4$ and $R^5$ are as defined above, or the salts thereof as its active component(s).

* * * * *

UNITED STATES PATENT AND TRADEMARK OFFICE
CERTIFICATE OF CORRECTION

PATENT NO. : 5,807,806
DATED : September 15, 1998
INVENTOR(S) : Katsunori Takana, et al.

It is certified that error appears in the above-identified patent and that said Letters Patent is hereby corrected as shown below:

On the title page, item [30], should show prior foreign application filed: Japan 171064/1997, filed 12/6/97.

Title Page of Patent should show cities of all inventors as "Kanagawa, Japan".

In Column 9 - 10, the formula shown at the top of the page should be corrected to read as follows:

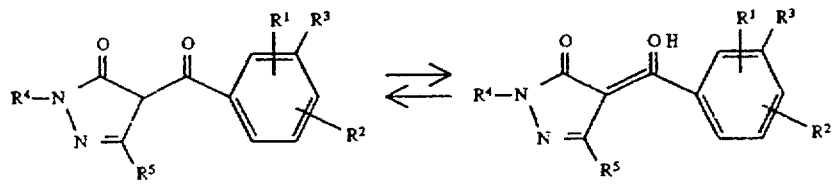

Column 31, Line 64 should be corrected to read as follows: "(1H,s), 7.30(1H,s),7.51(1H,d), 8.23(1H,d)"

UNITED STATES PATENT AND TRADEMARK OFFICE
CERTIFICATE OF CORRECTION

PATENT NO. : 5,807,806
DATED : September 15, 1998
INVENTOR(S) : Katsunori Takana, et al.

It is certified that error appears in the above-identified patent and that said Letters Patent is hereby corrected as shown below:

In Column 33, Line 51, the word "purauant" should be corrected to read "pursuant"

In Column 34, Line 1, the word "weed" should be corrected to read "weeds" in the first occurrence.

Signed and Sealed this

Twenty-third Day of March, 1999

Attest:

Q. TODD DICKINSON

*Attesting Officer*          *Acting Commissioner of Patents and Trademarks*

UNITED STATES PATENT AND TRADEMARK OFFICE
CERTIFICATE OF CORRECTION

PATENT NO. : 5,807,806
DATED : September 15, 1998
INVENTOR(S) : Katsunori Tanaka, et al.

It is certified that error appears in the above-identified patent and that said Letters Patent is hereby corrected as shown below:

On the title page, item [30], should show prior foreign application filed: Japan 171064/1997, filed 12/6/97.

Title Page of Patent should show cities of all inventors as "Kanagawa, Japan".

In Column 9 - 10, the formula shown at the top of the page should be corrected to read as follows:

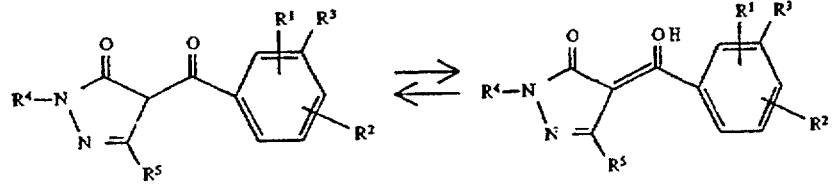

Column 31, Line 64 should be corrected to read as follows: "(1H,s), 7.30(1H,s), 7.51(1H,d), 8.23(1H,d)"

UNITED STATES PATENT AND TRADEMARK OFFICE
CERTIFICATE OF CORRECTION

PATENT NO. : 5,807,806
DATED : September 15, 1998
INVENTOR(S) : Katsunori Tanaka, et al.

It is certified that error appears in the above-identified patent and that said Letters Patent is hereby corrected as shown below:

In Column 33, Line 51, the word "purauant" should be corrected to read "pursuant"
In Column 34, Line 1, the word "weed" should be corrected to read "weeds" in the first occurrence.

This certificate supersedes Certificate of Correction issued March 23, 1999.

Signed and Sealed this

Seventh Day of December, 1999

Attest:

Q. TODD DICKINSON

Attesting Officer     Acting Commissioner of Patents and Trademarks